(12) United States Patent
Allen

(10) Patent No.: US 11,185,599 B2
(45) Date of Patent: *Nov. 30, 2021

(54) FORMATION AND USES OF EUROPIUM

(71) Applicant: WAYNE STATE UNIVERSITY, Detroit, MI (US)

(72) Inventor: Matthew J. Allen, Detroit, MI (US)

(73) Assignee: Wayne State University, Detroit, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/451,921

(22) Filed: Jun. 25, 2019

(65) Prior Publication Data

US 2020/0023082 A1 Jan. 23, 2020

Related U.S. Application Data

(62) Division of application No. 14/775,032, filed as application No. PCT/US2014/023283 on Mar. 11, 2014, now abandoned.

(Continued)

(51) Int. Cl.
| | |
|---|---|
| *A61K 9/00* | (2006.01) |
| *A61K 49/10* | (2006.01) |
| *A61K 49/18* | (2006.01) |
| *A61K 9/127* | (2006.01) |
| *C07F 5/00* | (2006.01) |

(52) U.S. Cl.
CPC ............ *A61K 49/101* (2013.01); *A61K 9/127* (2013.01); *A61K 49/106* (2013.01); *A61K 49/1812* (2013.01); *C07F 5/003* (2013.01)

(58) Field of Classification Search
CPC .................................................. A62K 49/101
See application file for complete search history.

(56) References Cited

U.S. PATENT DOCUMENTS

| | | |
|---|---|---|
| 2007/0292354 A1 | 12/2007 | Port |
| 2012/0213698 A1 | 8/2012 | Petersen |
| 2013/0078189 A1 | 3/2013 | Allen et al. |

FOREIGN PATENT DOCUMENTS

| | | |
|---|---|---|
| WO | 01/60417 A2 | 8/2001 |
| WO | 2006/032705 A2 | 3/2006 |

(Continued)

OTHER PUBLICATIONS

Garcia, European Journal of Inorganic Chemistry, 2012, 12, 2135-2140.*

(Continued)

*Primary Examiner* — Paul W Dickinson
(74) *Attorney, Agent, or Firm* — Brooks Kushman P.C.

(57) ABSTRACT

An MRI contrast composition includes a liposome and a europium metal complex disposed within the liposome. The europium metal complex includes a europium metal ion and a multi-dentate ligand selected from the group consisting of cryptands and thiacryptands and one or more counter-ions that balances a charge of the europium metal ion and the multi-dentate ligand, the europium metal ion being switchable between a 2+ and 3+ oxidation state. The contrast composition advantageously provides an oxidation-responsive dual-mode contrast agent because it would enhance either $T_1$-weighted images or CEST images depending on the oxidation state of Eu.

9 Claims, 9 Drawing Sheets

Related U.S. Application Data

(60) Provisional application No. 61/776,354, filed on Mar. 11, 2013.

(56) References Cited

FOREIGN PATENT DOCUMENTS

| WO | 2011/090977 A1 | 7/2011 | |
|---|---|---|---|
| WO | WO-2011090977 A1 * | 7/2011 | ............. C09B 57/10 |

OTHER PUBLICATIONS

Aime, S. et al., "Highly Sensitive MRI Chemical Exchange Saturation Transfer Agents Using Liposomes," Chem. Int. Ed. 2005, 44, 5513-5515.

Bottrill, M. et al., "Lanthanides in Magnetic Resonance Imaging," Chemical Society Reviews, 2006, v. 35, pp. 557-571.

Dua, J.S. et al, "Liposome: Methods of Preparation and Applications," International Journal of Pharmaceutical Studies and Research, vol. III/ Issue II/Apr.-Jun. 2012, p. 14-20.

Garcia, J. et al., "Physical Properties of Eu2+-Containing Cryptates as Contrast Agents for Ultrahigh-Field Magnetic Resonance Imaging," European J. of Inorganic Chem., v. 2012, n. 12, 2012, pp. 2135-2140.

Garcia, J. et al., "Eull-containing cryptates as contrast agents for ultra-high field strength magnetic resonance imaging," J. Chem. Commun. 2011, 47, 12858-12860.

Gianolio, E. et al., "Relaxometric Investigations and MRI Evaluation of a Liposome Loaded pH-Responsive Gadolinium(III) Complex," Inorg. Chem. 2012, 51, 7210-7217.

Placidi, M.P. et al., "Synthesis and spectroscopic studies on azo-dye derivatives of polymetallic lanthanide complexes: using diazotization to link metal complexes together," J. of the American Chemical Soc. 2009, v. 131, pp. 9916-9917.

European Search Report dated Oct. 18, 2016 for European Appn. No. 14779079.4, 7 pgs.

International Search Report dated Aug. 7, 2014 in PCT/US2014/023283 (filed Mar. 11, 2014), 4 pgs.

* cited by examiner

FORMATION AND USES OF EUROPIUM

CROSS-REFERENCE TO RELATED APPLICATIONS

This application is a divisional of U.S. patent application Ser. No. 14/775,032 filed Sep. 11, 2015, which is the U.S. national phase of PCT Application No. PCT/US2014/023283, filed Mar. 11, 2014, which claims the benefit of U.S. Ser. No. 61/776,354 Mar. 11, 2013, the disclosures of which are incorporated in their entirety by reference herein.

TECHNICAL FIELD

In at least one aspect, the present invention is related to magnetic resonance imaging contrast agents.

BACKGROUND

The power of magnetic resonance imaging (MRI) resides in the ability to ascertain anatomical information at high resolution (<1 mm$^3$). Molecular information can also be obtained with MRI using responsive paramagnetic complexes (contrast agents) that alter water proton signal intensities in response to chemical events. Some contrast agents respond to changes in pH, temperature, or metal ion concentration; enzyme activity; the presence of free radicals, antioxidants, phosphate diesters, or singlet oxygen; or changes in the partial pressure of oxygen. Of particular interest are targets that cause changes in redox behavior because they are associated with cancer, inflammation, and cardiovascular diseases. Therefore, responsive contrast agents that target redox changes have the potential to greatly improve the diagnostic capabilities of MRI. However, a critical limitation of responsive contrast agents that hinders their use in vivo is that determination of molecular information requires knowledge of the concentration of the contrast agents, which is exceedingly difficult to measure in vivo. Some systems have achieved concentration independence in contrast-enhanced MRI through ratiometric techniques (longitudinal vs transverse relaxation rates), ratiometric chemical exchange saturation transfer (CEST) techniques, or the use of orthogonal detection modes with a multimodal agent. However, no reported systems respond to general oxidizing events based on tunable redox potentials. An ideal metal for tunable multimodal redox response is Eu because the Eu$^{2+}$ and Eu$^{3+}$ oxidation states differentially enhance T$_1$-weighted and CEST images in MRI. Furthermore, Eu$^{2+}$ has a tunable oxidation potential and outperforms clinically approved T$_1$-shortening contrast agents at ultra-high magnetic field strengths.

Accordingly, there is a need for improved contrast agents for magnetic resonance imaging.

SUMMARY

In at least one embodiment, the present invention provides an MRI contrast composition. The composition includes a liposome and a europium metal complex disposed within the liposome. The europium metal complex includes a europium metal ion and a multi-dentate ligand selected from the group consisting of cryptands and thiacryptands and if necessary counter-ions to maintain charge neutrality (i.e., balances a charge of the europium metal ion and the multi-dentate ligand), the europium metal ion being switchable between a 2+ and 3+ oxidation state. The present embodiment advantageously provides an oxidation-responsive dual-mode contrast agent because it would enhance either T$_1$-weighted images or CEST images depending on the oxidation state of Eu.

In another embodiment, a MRI contrast compound is provided. The compound is described by formula (II):

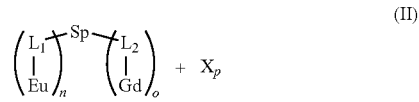

wherein:

n, o are each independently 1 or 2;

L$_1$ is a multi-dentate ligand moiety that bonds to Eu;

L$_2$ is a multi-dentate ligand moiety that bonds to Gd;

Xp are counter ions necessary to maintain charge neutrality; and

Sp is a spacer moiety that provides separation between Eu and Gd. Advantageously, compound II is useful as an MRI contrast agent whether or not it is encapsulated in a liposome.

In still another embodiment, a europium metal complex having formula (VIII) is provided:

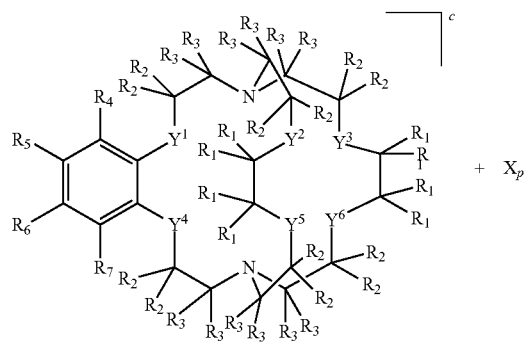

wherein:

c is the charge of the combination of the europium metal atom and the multi-dentate ligand;

Xp represents a number of counter-ions necessary for charge neutrality;

Y$^1$, Y$^2$, Y$^3$, Y$^4$, Y$^5$, and Y$^6$ are each independently O or S;

R$_1$, R$_2$, R$_3$ are each independently H, C$_{1-12}$ alkyl, C$_{1-12}$ alkynyl, C$_{1-12}$ alkenyl, C$_{1-12}$ fluoroalkyl, Cl, F, Br, nitro, cyano, or C$_{6-14}$ aryl, C$_{5-14}$ hetereoaryl, or 5 and 6 membered rings formed by combining R$_1$ on adjacent carbon atoms or R$_2$ and R$_3$ on adjacent carbon atoms, =O by combining R$_1$, R$_2$, or R$_3$ on the same carbon atom, =S by combining R$_1$, R$_2$, or R$_3$ on the same carbon atom, or =NR by combining R$_1$, R$_2$, or R$_3$ on the same carbon atom.

R is H or C$_{1-12}$ alkyl; and

R$_4$, R$_5$, R$_6$, R$_7$ are each independently hydrogen, cyano, nitro, Cl, F, Br, I, CH$_3$, NH$_2$, C$_{6-15}$ aryl, carboxylated C$_{6-18}$ aryl, C$_{5-15}$ heteroaryl, carboxylated C$_{5-18}$ heteroaryl, C$_{1-12}$ alkyl, phenyl, carboxylated phenyl, carboxylated C$_{2-12}$ alkyl, —CO$_2$H, —CH$_2$CO$_2$H,

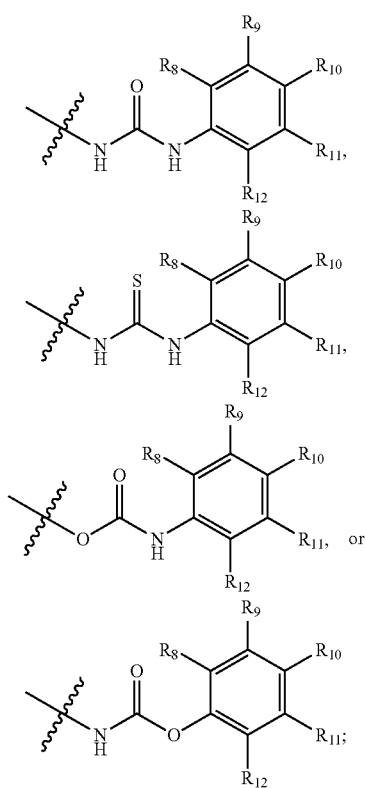

$R_8$, $R_9$, $R_{10}$, $R_{11}$, $R_{12}$ are each independently H or $CO_2H$. Advantageously, compound VIII is useful as an MRI contrast agent whether or not it is encapsulated in a liposome.

In another embodiment, a method of magnetic resonance imaging of an organ or organ structure in a subject is provided. The method includes a step of administering a liposome composition to the subject. The liposome composition includes a liposome and a europium metal complex disposed within the liposome. The europium metal complex includes a europium metal ion and a first multi-dentate ligand selected from the group consisting of cryptands and thiacryptands and one or more counter-ions that balance a charge of the europium metal ion. Images of an organ in the subject are taken by magnetic resonance imagining.

DETAILED DESCRIPTION

Figure 1:
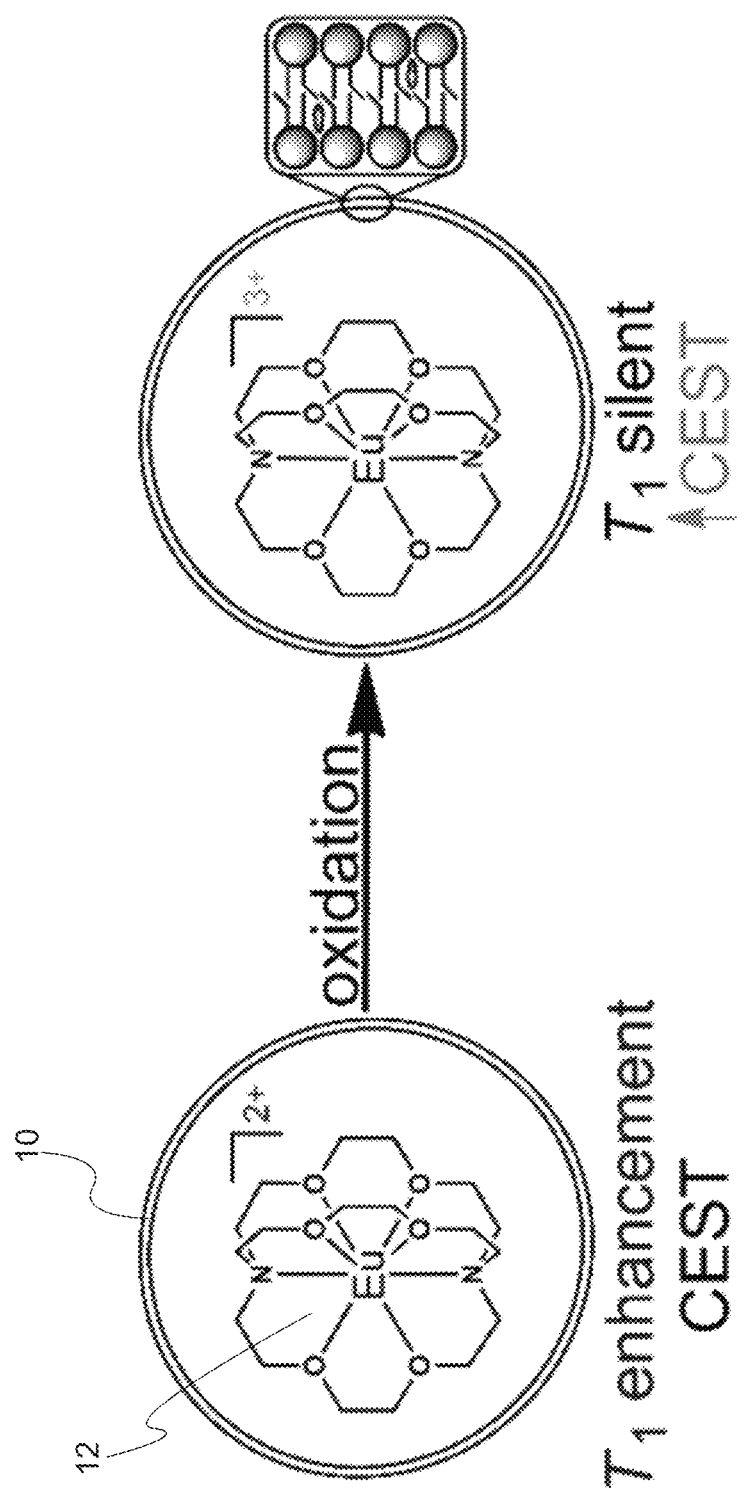
FIG. 1 provides a schematic representation of the oxidation of liposome-encapsulated Eu(2.2.2)2+ (T1 enhancement, CEST present) to form a liposome filled with $Eu^{3+}$ (T1 silent, increased CEST enhancement). On the far right is a depiction of the liposomal phospholipid bilayer with ovals as cholesterol molecules. For clarity, only one complex is shown in each liposome and coordinated water molecules are not drawn.

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property. Unless stated to the contrary, all R groups include H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, or $C_{5-14}$ heteroaryl.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "liposome" as used herein refers to artificially prepares membrane enclosed vesicle composed of bilayers of amphiphiles, which are characterized by having a hydrophilic and a hydrophobic group on the same molecule. Liposomes include one to several of these bilayers.

The term "alkyl", as used herein, unless otherwise indicated, includes $C_{1-12}$ saturated monovalent hydrocarbon radicals having straight or branched moieties, including, but not limited to, methyl, ethyl, n-propyl, iso-propyl, n-butyl, sec-butyl, tert-butyl, and the like.

The term "alkenyl", as used herein, unless otherwise indicated, includes $C_{2-12}$ alkyl groups, as defined above, having at least one carbon-carbon double bond, such as —$CH_2$—$CH$=$CH_2$.

The term "alkynyl", as used herein, unless otherwise indicated, includes $C_{2-12}$ alkyl groups, as defined above, having at least one carbon-carbon triple bond, such as —$CH_2C$≡$CH$.

The term "alkylenyl", as used herein, unless otherwise indicated, includes $C_{1-12}$ saturated divalent hydrocarbon radicals having straight or branched moieties.

The term "cryptand" as used herein mean a bi- and polycyclic polyazo-polyether multi-dentate ligand, where three-coordinate nitrogen atoms provide the vertices of a three-dimensional structure.

The term "thiacryptand" as used herein mean a cryptand with at least one oxygen atom replaced by a sulfur atom.

The term "carboxylated" as used herein means that a chemical moiety is substituted with $CO_2H$ (or $CO_2^-$).

The term "subject" refers to a human or animal, including all mammals such as primates (particularly higher primates), sheep, dog, rodents (e.g., mouse or rat), guinea pig, goat, pig, cat, rabbit, and cow.

Figure 2:
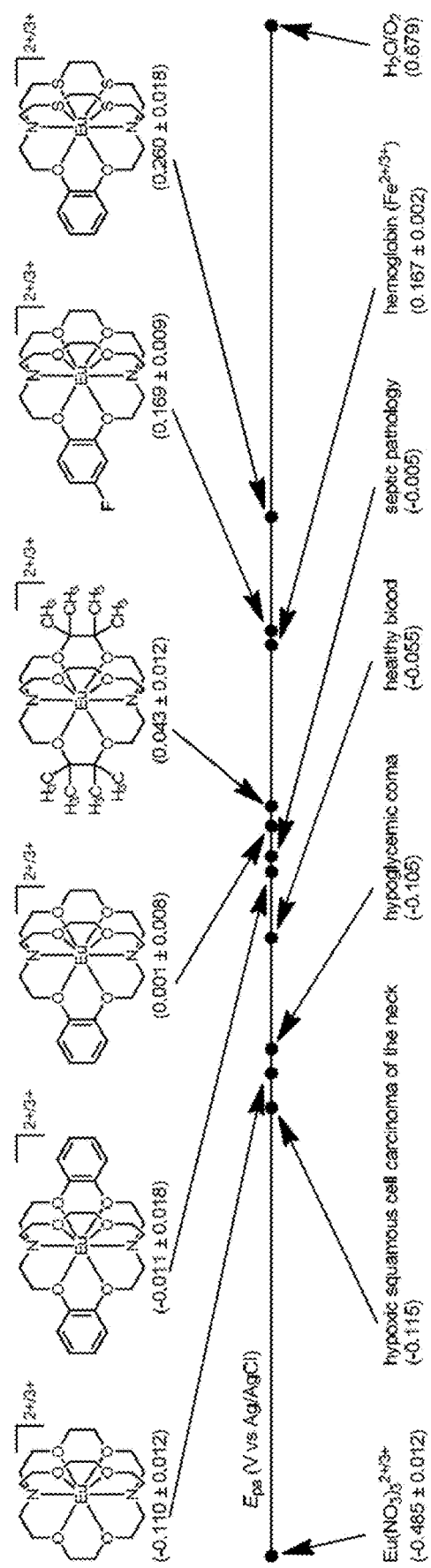
FIG. 2 provides oxidations potential for various europium/cryptand complexes.

In an embodiment, a composition useful for magnetic resonance imaging applications is provided. The composition includes a plurality of liposomes, europium (Eu) metal complexes disposed within the liposomes. Each europium metal complex including a europium metal ion and a first multi-dentate ligand selected from the group consisting of cryptands and thiacryptands. The composition also includes if necessary counter ions to maintain charge neutrality (e.g., one or more counter-ions that balance the charge of the europium metal ion and the multi-dentate ligand). The europium metal atom typically has a formal charge of +2 or +3 depending on the oxidation state. Depending on the substitutes on the multi-dentate ligand, the ligand may also have a formal charge under physiological conditions. For example, carboxylates may have a negative charge under physiological conditions. The counter-ions render the europium metal complex neutral. Examples of counter-ions when the combination of europium metal atom and multi-dentate ligand are positive include, but are not limited to, halide, hydroxide, bicarbonate, phosphate, and the like. Examples of counter-ions when the combination of europium metal atom and multi-dentate ligand are negative include, but are not limited to, alkali metal ions (e.g., $Na^+$, $K^+$), $H^+$, other metal ions, and the like. FIG. 1 illustrates a liposome 10 encapsulating europium metal complex 12. Surprisingly, the europium metal ions are switchable between a 2+ and 3+ oxidation state even when encapsulated in the liposome as illustrated in FIG. 1. The oxidation of $Eu^{2+}$ to $Eu^{3+}$ provides orthogonal modes of detection by MRI. The $Eu^{2+/3+}$ oxidation state switch offers an ideal platform for oxygen-responsive contrast enhancement. In the variations and refinements set forth below, changes to ligand structure made the corresponding oxidation potential of $Eu^{2+}$ tunable over a physiologically relevant range. For example, FIG. 2 provides the oxidation potential for several complexes thereby demonstrating the tenability and stability of these compounds. The encapsulation of the europium metal complexes in liposomes advantageously provides concentration-independent diagnostic imaging of redox-active disease states using the chemistry of Eu.

Typically, each liposome includes a phospholipid such as fatty acid di-esters of phosphatidylcholine, ethylphosphatidylcholine, phosphatidylglycerol, phosphatidic acid, phosphatidylethanolamine, phosphatidylserine or sphingomyelin. A particularly useful phospholipid is 1-palmitoyl-2-oleoyl-sn-glycero-3-phosphocholine. In many useful variations, the composition also includes a pharmaceutically acceptable aqueous carrier such as an aqueous buffer. In a refinement, the liposomes have an average diameter less than about 200 nm. In still other refinements, the liposomes have an average diameter less than about, in increasing order of preference, 200 nm, 150 nm, 130 nm, 120 nm, and 100 nm. In yet other refinements, the liposomes have an average diameter greater than about, in increasing order of preference, 40 nm, 50 nm, 60 nm, 70 nm, and 80 nm.

The europium metal complex may be included in the liposomes by any of the methods known to those skilled in the art for including drugs into liposomes. Examples of such techniques are set forth in J. S. Dua et al., *Liposome: Methods of Preparation and Applications*, International Journal of Pharmaceutical Studies and Research, Vol. III/Issue II/April-June (2012), p. 14-20; the entire disclosure of which is hereby incorporated by reference. In general, an aqueous solution of the europium metal complex set forth above is combined with a liposome forming precursor or a preformed liposome resulting in inclusion of the complex in the cavity of the liposome. Specific methods for forming the liposomes and incorporating the europium metal complex into the liposome include, but are not limit to, the thin-film hydration method, the ether injection method, ethanol injection method, detergent removal method, and the like. In a refinement, the liposomes are unilamellar. In another refinement, the liposomes are multilamellar. In some refinements, the liposomes further include additional amphiphilic compound such as cholesterol.

In a variation, the multi-dentate ligand is a substituted 2.2.2-Cryptand, an unsubstituted 2.2.2-Cryptand, a substituted 2.2.2-thiacryptand, or an unsubstituted 2.2.2-thiacryptand. It should be pointed out that the europium metal complexes used herein are oxidatively stable in aqueous medium with the degree of stabilization being dependent on the substituents on the cryptand. In this variation, the multi-dentate ligand is generally described by formula I:

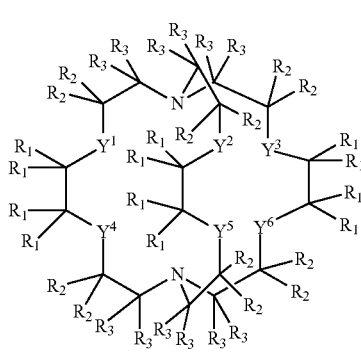

Figure 3:
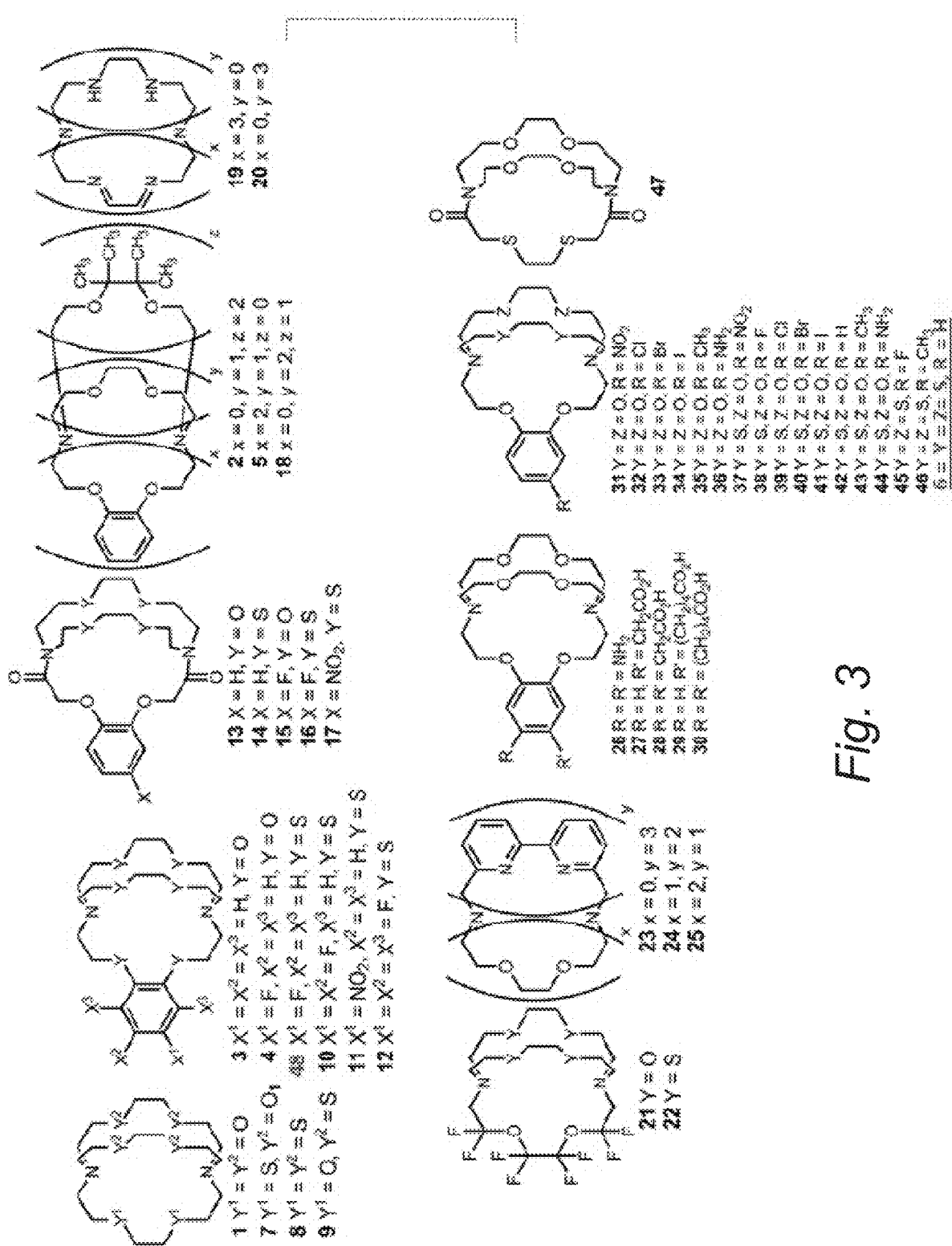
FIG. 3 provides specific examples of cryptands and thiacryptands that are useful as multi-dentate ligands in forming europium complexes.
Figure 4:
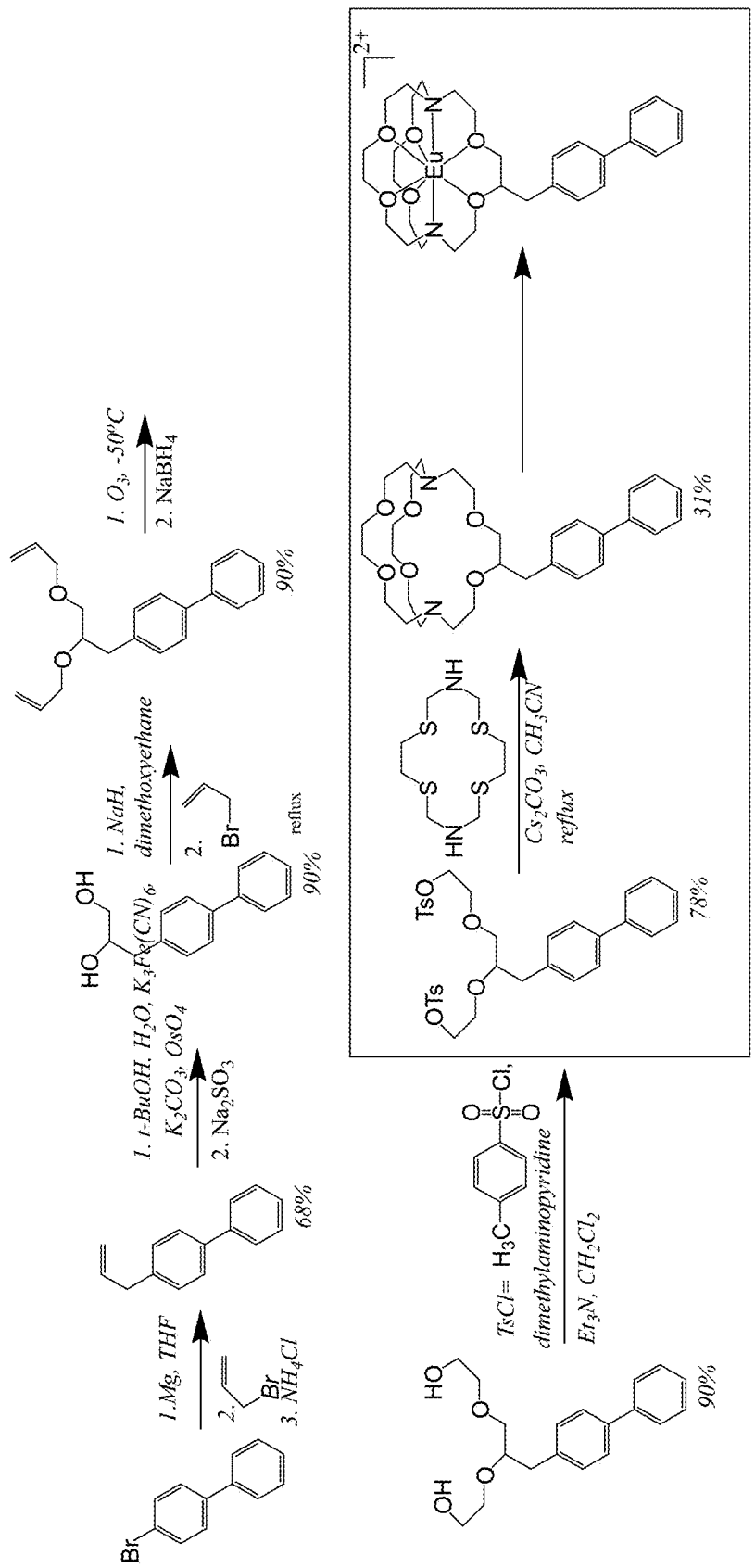
FIG. 4 provides synthetic pathways for forming cryptands that are useful as multi-dentate ligands in forming europium complexes.
Figure 5:
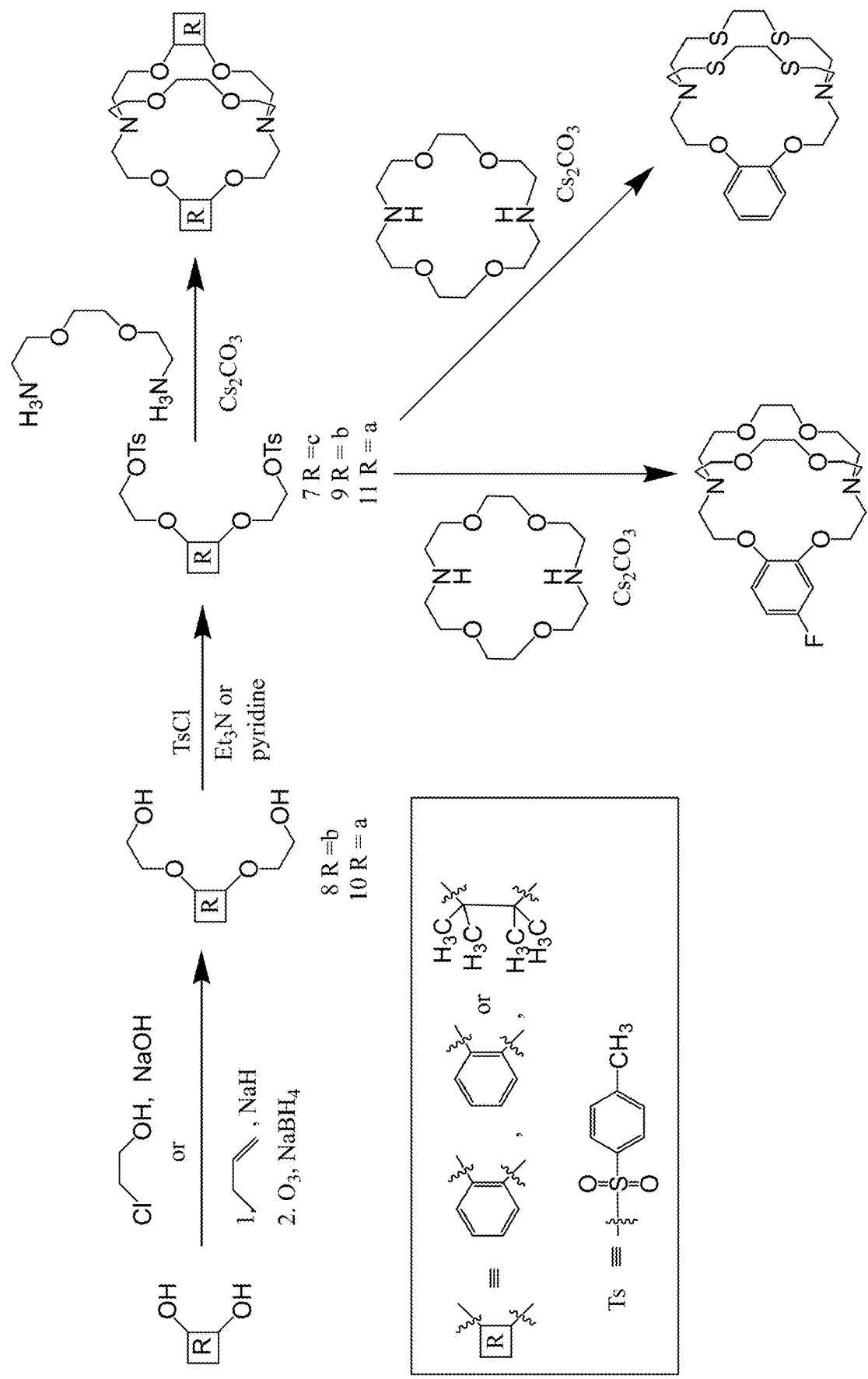
FIG. 5 provides specific examples of cryptands and thiacryptands that are useful as multi-dentate ligands in forming europium complexes.

(I)

wherein:
$Y^1$, $Y^2$, $Y^3$, $Y^4$, $Y^5$, and $Y^6$ are each independently O or S; $R_1$, $R_2$, $R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom; and
R is H or $C_{1-12}$ alkyl. It should be appreciated that in accordance with this terminology the $R_1$ may be different from each other, the $R_2$ may be different from each other, and the $R_3$ may be different from each other. In a refinement, $R_1$ on adjacent carbon atoms or $R_2$ and $R_3$ on adjacent carbon atoms form a phenyl group. In another refinement, $R_1$, $R_2$, or $R_3$ are each independently H, phenyl, or biphenyl. In some refinements, $R_2$ and $R_3$ are hydrogen and one of the $R_1$ is not hydrogen. In other refinements, $R_2$ and $R_3$ are hydrogen and two of the $R_1$ are not hydrogen. Examples of cryptands and thiacryptands and europium complexes including these moieties that useful in the compositions of the present invention are set forth in U.S. Pat. Pub. No. 20130078189 and in J. Garcia et al., *Physical Properties of $Eu^{2+}$-Containing Cryptates as Contrast Agents for Ultra-high-Field Magnetic Resonance Imaging, Eur. J. Inorg. Chem.* 2012, 2135-2140; the entire disclosures of which are hereby incorporated by reference in their entirety. FIG. 3 provides specific examples of cryptands and thiacryptands that are useful as multi-dentate ligands in the present invention. FIGS. 4 and 5 provide synthetic pathways for preparing some of the Eu complexes of the present embodiment. The following formula provides a representation of the Eu complex with the ligand of formula I:

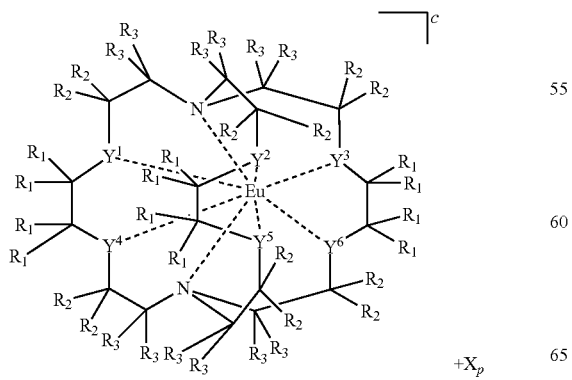

where c is the charge of the combination of the europium metal atom and the multi-dentate ligand. In a refinement, c is from −3 to +3. When the multi-dentate ligand is neutral, c is 2 or 3. Xp represents a number of counter-ions necessary for charge neutrality. X is a counter-ion as set forth above and p is the number of counter-ion necessary for charge neutrality. Typically, p is an integer from 0 to 3.

In a variation of the present embodiment, the composition further includes an antioxidant. The inclusion of an antioxidant limits the toxicity of europium metal complexes and improves the stability (i.e., oxidative stability). Both in vitro ($T^1$-based assays in the air) and in vivo (maximum tolerated dose assays coupled with biodistribution studies) studies can be used to evaluate the toxicity of the complexes. Examples of antioxidants include, but are not limited to, glutathione, 2-mercaptoethanol, dithiothreitol, S-adenosylmethionine, dithiocarbamate, dimethylsulfoxide, cysteine, methionine, cysteamine, oxo-thiazolidine-carboxylate, timonacic acid, malotilate, 1,2-dithiol 3-thione, 1,3-dithiol 2-thione, lipoamide, sulfarlem, oltipraz, taurine, N-acetylcysteine, and combinations thereof.

Additional examples of the multi-dentate ligand are described by the following formulae:

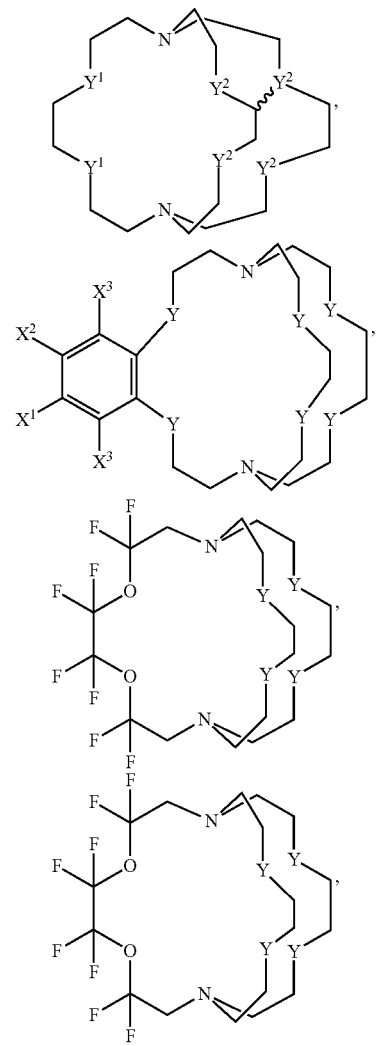

-continued

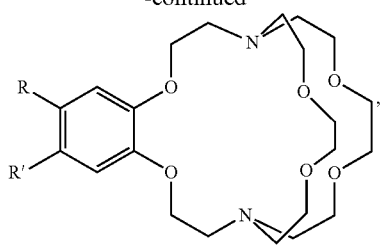

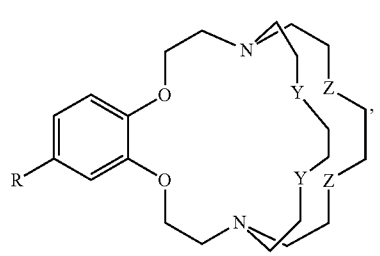

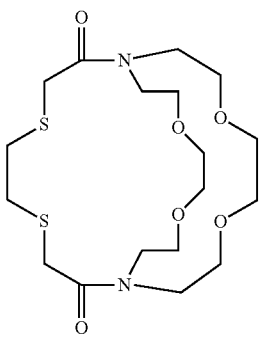

wherein Y, Z, Y$^1$ and Y$^2$ are each independently O or S; X$^1$, X$^2$, X$^3$ are independently nitro, Cl, F, Br, I, CH$_3$, NH$_2$, or CH$_2$CO$_2$H; and R, R' are independently nitro, Cl, F, Br, I, CH$_3$, NH$_2$, or CH$_2$CO$_2$H.

Another example of the multi-dentate ligand has the following formula:

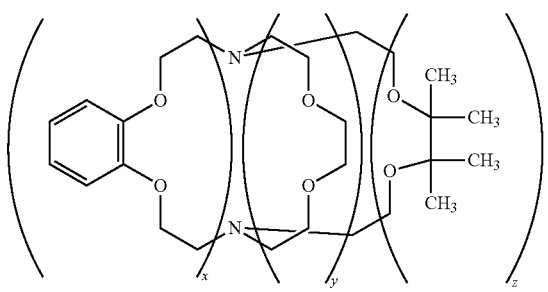

wherein x, y, and z are 0, 1, 2, or 3 with the proviso that the sum of x, y, and z is 3.

Another example of the multi-dentate ligand has the following formula:

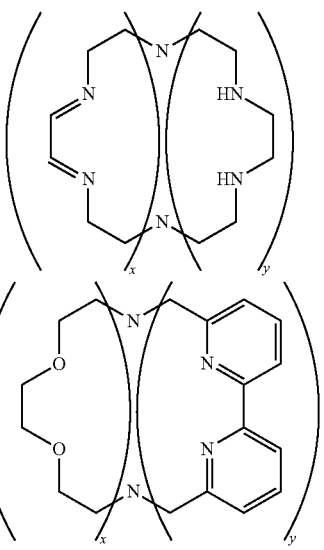

wherein x and y are 0, 1, 2, or 3 with the proviso that the sum of x and y is 3.

In another embodiment, a compound useful as an MRI contrast agent having formula II is provided:

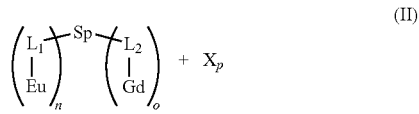

(II)

wherein:
n, o are each independently 1 or 2;
L$_1$ is a multi-dentate ligand that bonds to Eu;
L$_2$ is a multi-dentate ligand that bonds to Gd;
X is a counter-ion as set forth above and p is the number of counter-ion necessary for charge neutrality. Typically, p is an integer from 0 to 3; and
Sp is a spacer moiety that provides separation between Eu and Gd. Typically, Sp includes —(CH$_2$)$_n$—, C$_{2-12}$ alkylenyl, C$_{2-12}$ alkynyl, C$_{6-12}$ aryl, C$_{5-12}$ heteroaryl, urea groups (—NHCO—NH—), thiourea groups (—NHCSNH—), carbamate groups (—NHCOO—), C$_{1-10}$ amine groups, OH groups, NH groups C$_{1-10}$ alkenyl groups, and combinations thereof where n is 1 to 12. In a refinement, the compound having formula (II) is disposed with a liposome as set forth above.

Examples of Sp include:

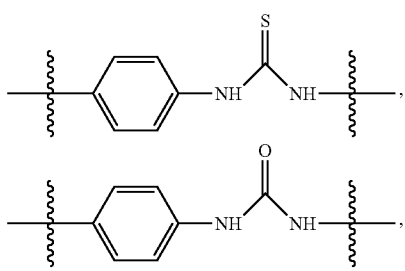

—(CH$_2$)$_n$—HNCONH—, —(CH$_2$)$_n$—HNCSNH—, and —(CH$_2$)$_n$—. In a variation, L$_1$ is described by the following formula:

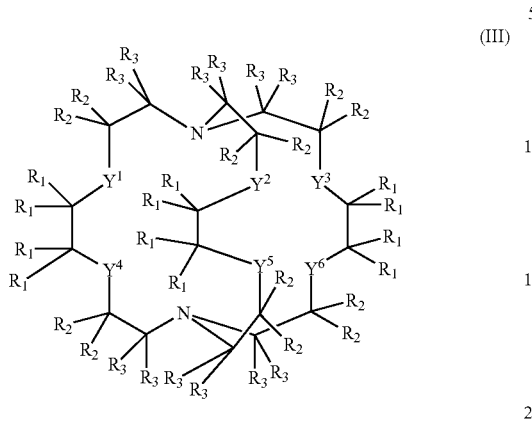

(III)

with at least one R$_1$, R$_2$, or R$_3$ being a bond to Sp or having a bond to Sp. Y$^1$, Y$^2$, Y$^3$, Y$^4$, Y$^5$, and Y$^6$ are each independently O or S; R$_1$, R$_2$, R$_3$ are each independently H, C$_{1-12}$ alkyl, C$_{1-12}$ fluoroalkyl, Cl, F, Br, nitro, cyano, or C$_{6-14}$ aryl, C$_{5-14}$ hetereoaryl, or 5 and 6 membered rings formed by combining R$_1$ on adjacent carbon atoms or R$_2$ and R$_3$ on adjacent carbon atoms, =O by combining R$_1$, R$_2$, or R$_3$ on the same carbon atom, =S by combining R$_1$, R$_2$, or R$_3$ on the same carbon atom, or =NR by combining R$_1$, R$_2$, or R$_3$ on the same carbon atom; and R is H or C$_{1-12}$ alkyl. In a refinement, R$_1$ on adjacent carbon atoms or R$_2$ and R$_3$ on adjacent carbon atoms form a phenyl group. In another refinement, R$_1$, R$_2$, R$_3$ are each independently H, phenyl, or biphenyl. In a variation, L$_2$ include a plurality of groups having formula IV:

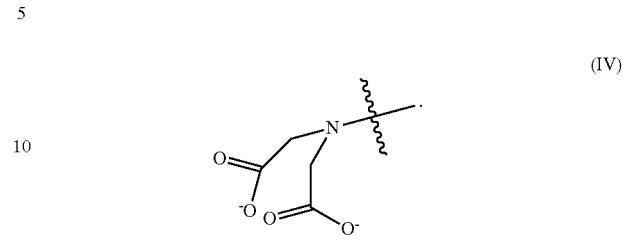

(IV)

In a refinement, L$_2$ includes a moiety having the following formula:

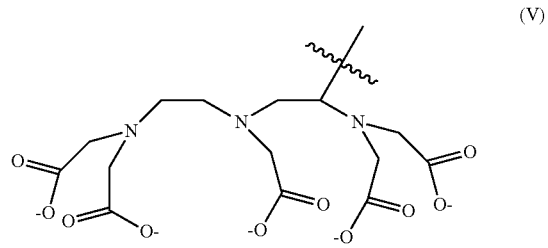

(V)

Specific examples of compounds having formula (II) are the following compounds:

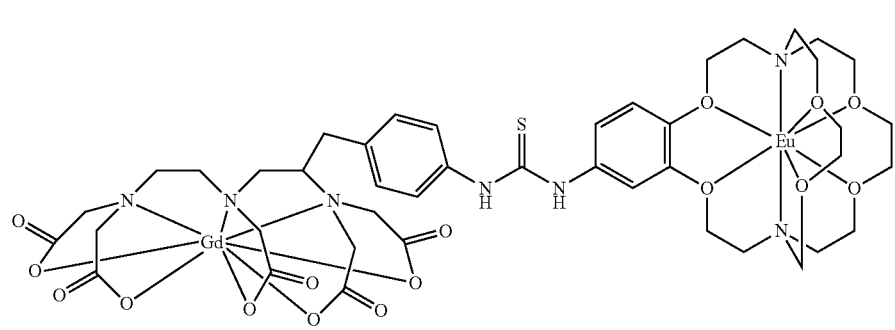

VI

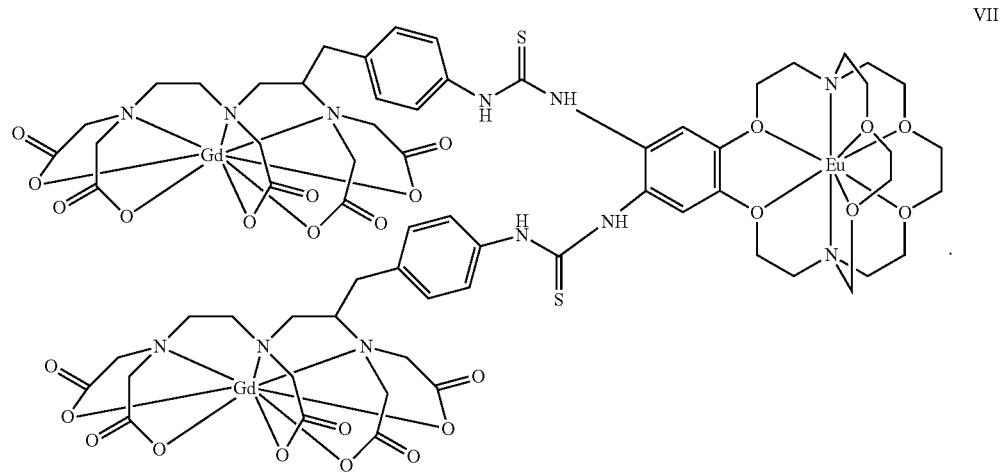

VII

It should be appreciated that the compounds of the present embodiment are capable of functioning as "universal field" agents that works at both low field and high field instruments.

In another embodiment, a europium metal complex comprising a europium metal ion, a multi-dentate having formula VIII, and if necessary counter-ions to maintain charge neutrality is provided:

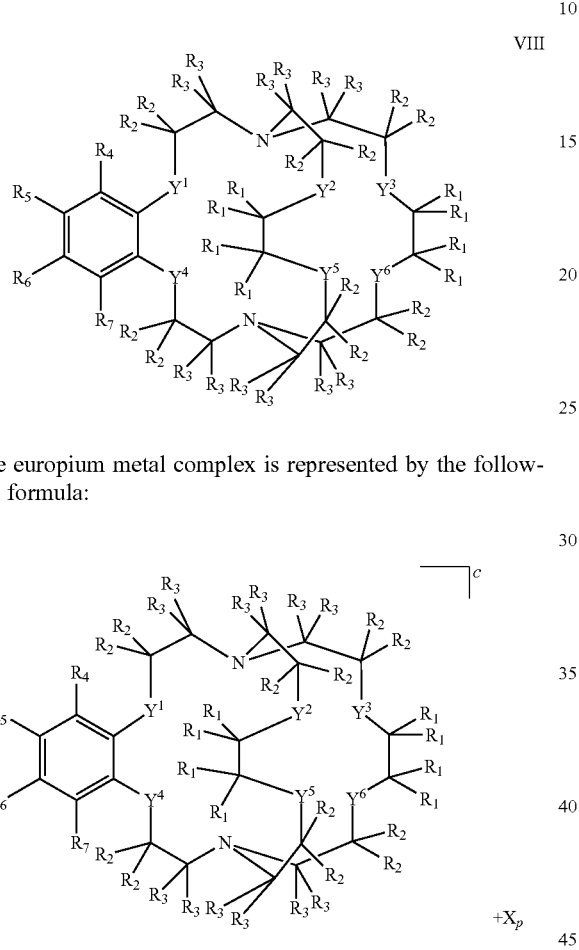

The europium metal complex is represented by the following formula:

wherein:
c is the charge of the combination of the europium metal atom and the multi-dentate ligand. In a refinement, c is from −3 to +3. When the multi-dentate ligand is neutral, c is 2 or 3. Xp represents a number of counter-ions necessary for charge neutrality. X is a counter-ion as set forth above and p is the number of counter-ion necessary for charge neutrality. Typically, p is an integer from 0 to 3; $Y^1$, $Y^2$, $Y^3$, $Y^4$, $Y^5$, and $Y^6$ are each independently O or S;
$R_1$, $R_2$, $R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ heteroaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom;
R is H or $C_{1-12}$ alkyl. In a refinement, $R_1$, $R_2$, or $R_3$ on adjacent carbon atoms or $R_2$ and $R_3$ on adjacent carbon atoms form a phenyl group. In another refinement, $R_1$, $R_2$, or $R_3$ are each independently H, phenyl, or biphenyl; and $R_4$, $R_5$, $R_6$, $R_7$ are each independently hydrogen, cyano, nitro, Cl, F, Br, I, $CH_3$, $NH_2$, $C_{6-15}$ aryl, carboxylated $C_{6-18}$ aryl, $C_{5-15}$ heteroaryl, carboxylated $C_{5-18}$ heteroaryl, $C_{1-12}$ alkyl, phenyl, carboxylated phenyl, carboxylated $C_{2-12}$ alkyl, —$CO_2H$, —$CH_2CO_2H$,

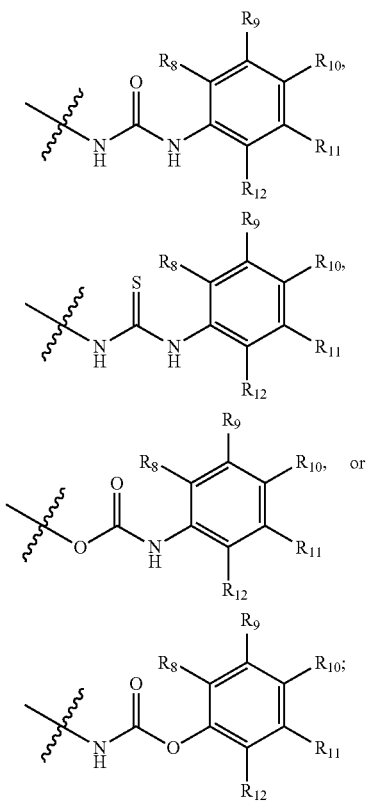

$R_8$, $R_9$, $R_{10}$, $R_{11}$, $R_{12}$ are each independently H or $CO_2H$. In should be appreciated that these compounds can be encapsulated in liposomes as set forth above. Refinements of the present embodiment are useful as "ultra-high field" T1 imaging agents.

In another embodiment, a europium metal complex comprising a europium metal ion, a multi-dentate having formula IX, and if necessary counter-ions to maintain charge neutrality is provided:

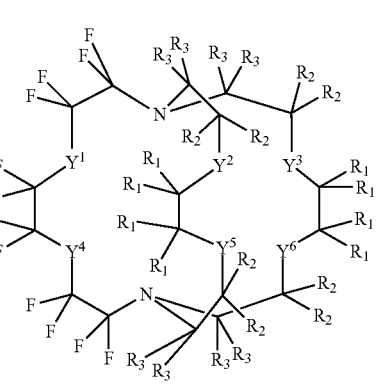

The europium metal complex is represented by the following formula:

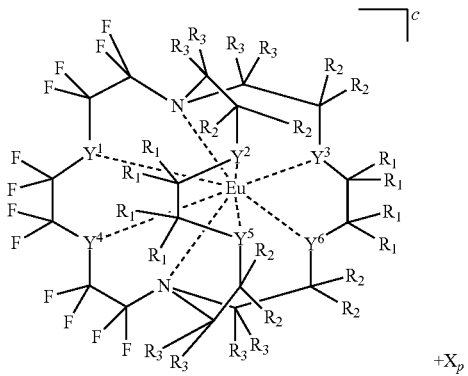

+X$_p$ wherein:

c is the charge of the combination of the europium metal atom and the multi-dentate ligand. In a refinement, c is from −3 to +3. When the multi-dentate ligand is neutral, c is 2 or 3. Xp represents a number of counter-ions necessary for charge neutrality. X is a counter-ion as set forth above and p is the number of counter-ion necessary for charge neutrality. Typically, p is an integer from 0 to 3;

$Y^1$, $Y^2$, $Y^3$, $Y^4$, $Y^5$, and $Y^6$ are each independently O or S;

$R_1$, $R_2$, $R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom; and R is H or $C_{1-12}$ alkyl. In a refinement, $R_1$ on adjacent carbon atoms or $R_2$ and $R_3$ on adjacent carbon atoms form a phenyl group. In another refinement, $R_1$, $R_2$, or $R_3$ are each independently H, phenyl, or biphenyl. In should be appreciated that these compounds can be encapsulated in liposomes as set forth above.

In another embodiment, a europium metal complex comprising a europium metal ion, a multi-dentate having formula X, and if necessary counter-ions to maintain charge neutrality is provided:

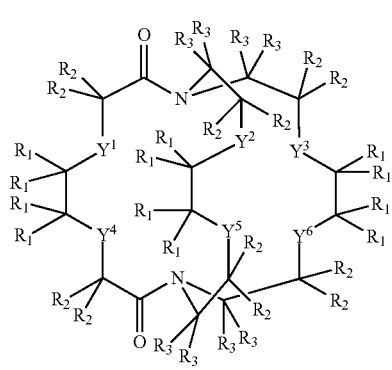

(X)

The europium metal complex is represented by the following formula:

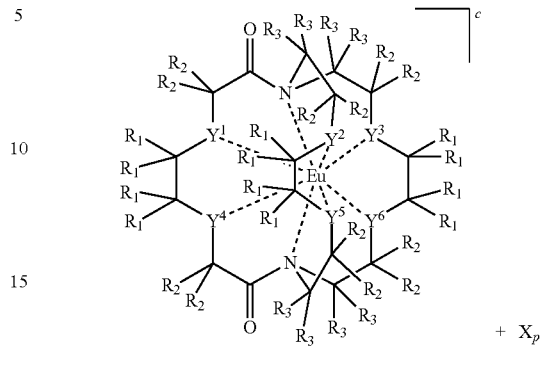

+ X$_p$ wherein:

c is the charge of the combination of the europium metal atom and the multi-dentate ligand. In a refinement, c is from −3 to +3. When the multi-dentate ligand is neutral, c is 2 or 3. Xp represents a number of counter-ions necessary for charge neutrality. X is a counter-ion as set forth above and p is the number of counter-ion necessary for charge neutrality. Typically, p is an integer from 0 to 3;

$Y^1$, $Y^2$, $Y^3$, $Y^4$, $Y^5$, and $Y^6$ are each independently O or S;

$R_1$, $R_2$, $R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom; and R is H or $C_{1-12}$ alkyl. In a refinement, $R_1$ on adjacent carbon atoms or $R_2$ and $R_3$ on adjacent carbon atoms form a phenyl group. In another refinement, $R_1$, $R_2$, or $R_3$ are each independently H, phenyl, or biphenyl. In should be appreciated that these compounds can be encapsulated in liposomes as set forth above.

In another embodiment, a method of magnetic resonance imaging of an organ or organ structure in a subject. $Eu^{2+}$-based complexes encapsulated inside liposomes can be detected with conventional $T_1$-weighted MR imaging while oxidation to $Eu^{3+}$ will result in a contrast agent that can be detected with paramagnetic chemical exchange saturation transfer (PARACEST) imaging. The method includes a step of administering a liposome composition to the subject and then taking images of the organ of interest in the subject by magnetic resonance imaging. The liposome composition including a liposome; and a europium metal complex disposed within the liposome. The europium metal complex includes a europium metal ion and a first multi-dentate ligand selected from the group consisting of cryptands and thiacryptands, and one or more counter-ions that balances the charge of the europium metal ion. The details of the liposome, europium metal complex, and the multi-dentate ligands are set forth above. In one refinement, the magnetic resonance imaging is $T_1$-weighted imaging. In another refinement, the magnetic resonance imaging is by chemical exchange saturation transfer (CEST) and in particular, PAR-ACEST. In still another refinement, the method tracks the migration of the contrast agent with $T_1$-weighted imaging and then upon disappearance of $T_1$ enhancement, the imaging mode of detection is changed to CEST. In this these refinements, the presence of CEST would indicate oxidation, and an absence of CEST enhancement would indicate clearance of the contrast agent. Furthermore, CEST enhancement could be used to indicate one or more specific disease states because the oxidation potential, and consequently loss of $T_1$ enhancement, of $Eu^{2+}$ is tunable through ligand structure modifications. In general, the magnetic resonance imaging involves positioning the subject in a magnetic field typically having a spatial gradient. AN electromagnetic pulse (i.e., radiofrequency pulse) is applied to the subject with the frequency being varied over a region where hydrogen atoms resonate. At the resonance frequency for the water hydrogen atoms in the spatial region being scanned, absorption occurs with the signal subsequently emitted being monitored to provide the $T_1$-weighted image. In CEST imaging, the hydrogen atoms for water in the liposomes are brought to saturation by the applied electromagnetic pulse. The resulting magnetization is transferred to mobile water molecules outside of the liposomes with the emission from the hydrogen atoms on these mobile water molecules being monitored to provide the data required for CEST imaging.

The Examples below are included to demonstrate preferred embodiments of the invention. It should be appreciated by those of skill in the art that the techniques disclosed in the Examples represent techniques and compositions discovered by the inventors to function well in the practice of embodiments disclosed herein, and thus can be considered to constitute preferred modes for its practice. However, those of skill in the art should, in light of the present disclosure, appreciate that many changes can be made in the specific embodiments which are disclosed and obtain a like or similar result without departing from the spirit and scope of embodiments disclosed herein.

The compositions set forth above use liposomes because their aqueous inner cavity can encapsulate water-soluble contrast agents to improve the sensitivity of CEST by increasing the ratio of chemically shifted water protons (inside liposomes) to bulk water protons (outside liposomes) (Aime, S.; Castelli, D. D.; Terreno, E. Angew. Chem. Int. Ed. 2005, 44, 5513-5515). Liposome composition was adapted from a report that used 1-palmitoyl-2-oleoyl-sn-glycero-3-phosphocholine and cholesterol (Gianolio, E.; Porto, S.; Napolitano, R.; Baroni, S.; Giovenzana, G. B.; Aime, S. Inorg. Chem. 2012, 51, 7210-7217), and liposomes were characterized using dynamic light scattering. The average diameter measured before and after air exposure was 110±7 and 106±7 nm, respectively, where the error is the standard error calculated from the average polydispersity index values. The average liposome polydispersity index value before and after air exposure was 0.14±0.01 and 0.10±0.06, respectively, where the polydispersity index error is the standard error at the 95% confidence interval. These size distribution data indicate that average liposome size was not different before and after oxidation (Student t test) and, consequently, not affected by the intraliposomal formation of $Eu^{3+}$.

To evaluate the response of our liposomes, suspensions of liposomes containing $Eu(2.2.2)^{2+}$ were measured before and after exposure to air and observed $T_1$ lengthening upon air exposure (0.4 and 2.8 s before and after air exposure, respectively, 24° C., 11.7 T, 45 mM Eu). This observation is in good agreement with the $T_1$-shortening nature of $Eu(2.2.2)^{2+}$ (Garcia, J.; Neelavalli, J.; Haacke, E. M.; Allen, M. J. Chem. Commun. 2011, 47, 12858-12860 and Garcia, J.; Kuda-Wedagedara, A. N. W.; Allen, M. J. Eur. J. Inorg. Chem. 2012, 2012, 2135-2140) and indicates that oxidation to form $Eu^{3+}$ caused the observed lengthening of $T_1$. Furthermore, the data suggest the water-exchange rate between intraliposomal and bulk water is sufficiently fast for positive contrast enhancement.

Figure 6:
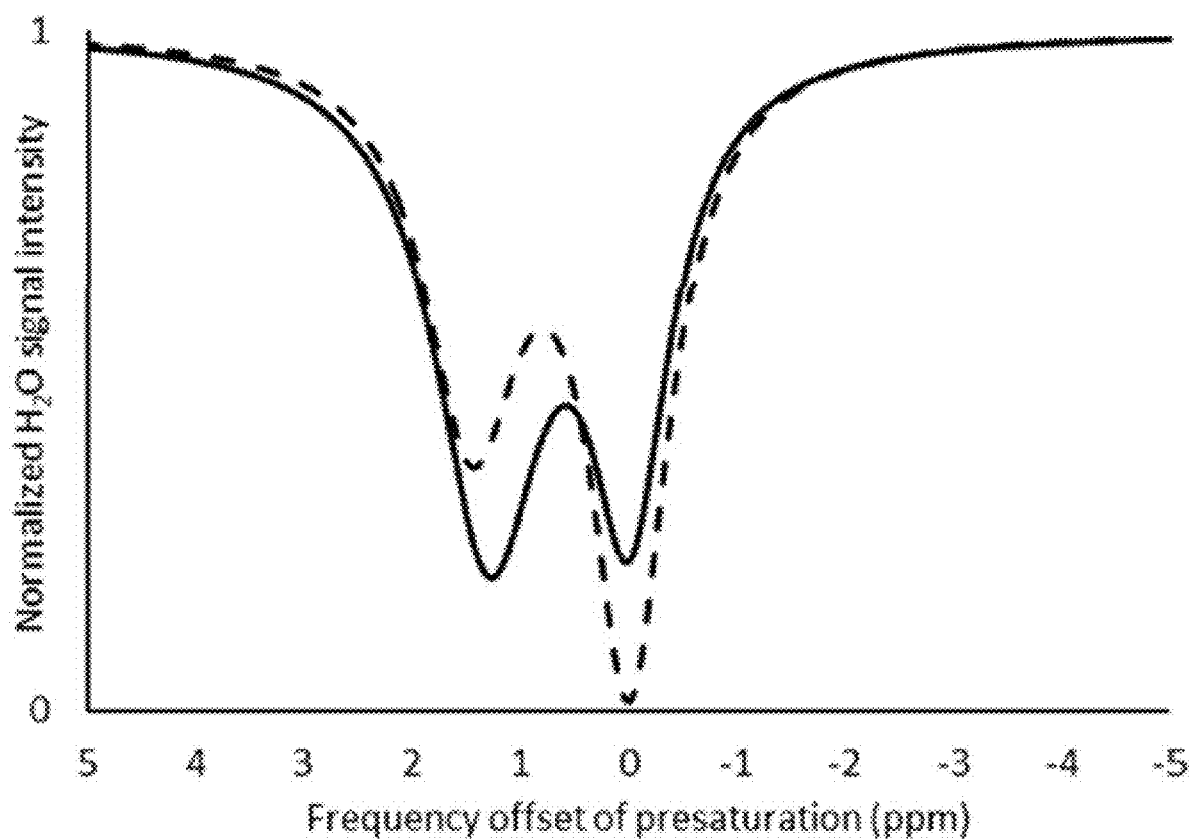
FIG. 6 provides Lorentzian-fitted CEST spectra (7 T, ambient temperature) of liposomes before (dashed line) and after (solid line) air exposure. Bulk water was referenced to 0 ppm and signal intensities were calculated from in vitro images after a 2 s presaturation with a 17 μT radiofrequency pulse from 5 to −5 ppm in 0.2 ppm increments.

To characterize the dual-mode behavior of Eu-containing liposomes, response were measured before and after air exposure using in vitro image intensities as a function of frequency offset of presaturation at 7 T. The intensity data was fitted with a Lorentzian function using least squares fitting to reference bulk water to 0 ppm (FIG. 6). Lorentzian fitting was used because the sample images were acquired simultaneously and the bulk water signals were not centered at 0 ppm likely due to inhomogeneities in the magnetic field. Interestingly, saturation of the bulk water signal after air exposure was not observed. The CEST spectrum revealed that liposomes before and after 24 hour air exposure had exchangeable intraliposomal water protons at 1.4 and 1.2 ppm, respectively, relative to bulk water. A possible explanation for the observation of CEST both before and after oxidation is that a difference in osmolality between intraliposomal and bulk water caused osmotic shrinking of liposomes. Intraliposomal osmolality influences the chemical shift of intraliposomal water protons, and this phenomenon has been demonstrated for $Gd^{3+}$-containing liposomes.

Figure 7:
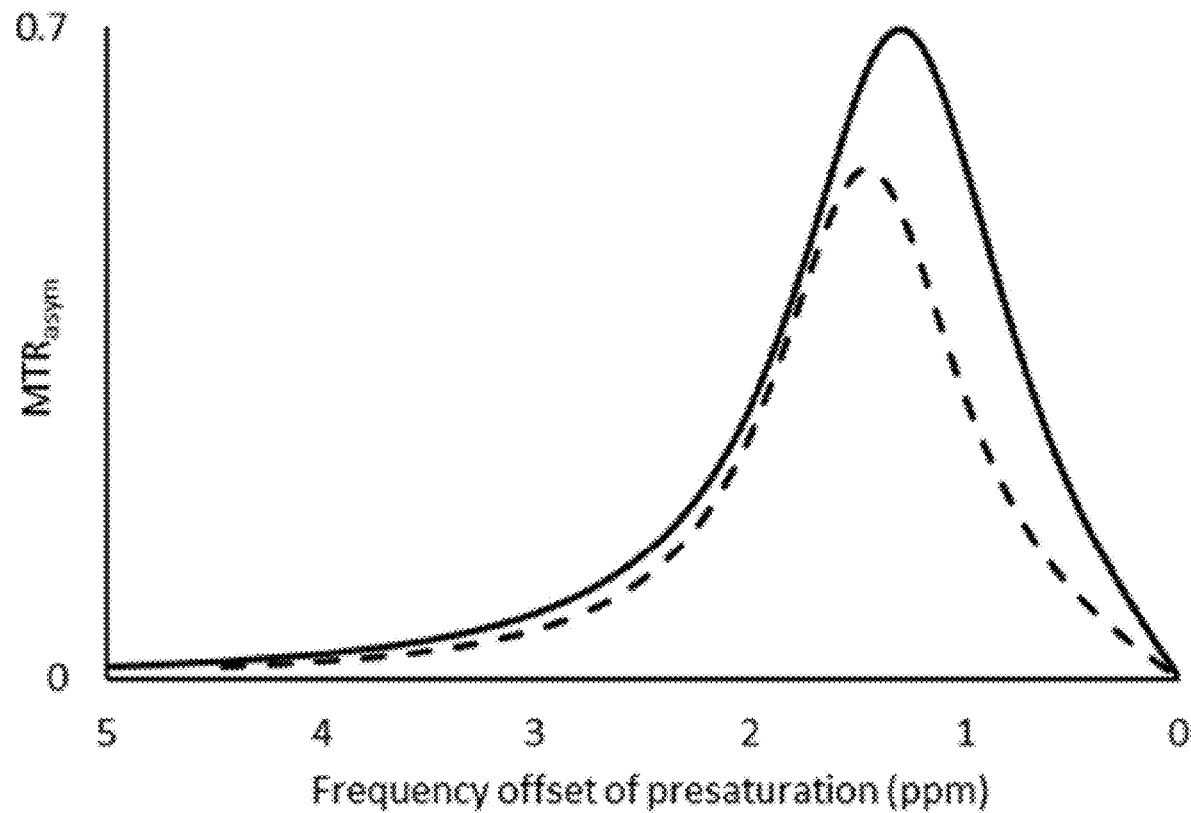
FIG. 7 provides a $MTR_{asym}$ vs frequency offset of presaturation for liposomes before (dashed line) and after (solid line) air exposure. $MTR_{asym}$ was calculated using fitted Lorentzian functions.

A magnetization transfer ratio asymmetry analysis ($MTR_{asym}$, FIG. 7) was performed because the exchangeable signals appeared partially overlapped with the bulk water signal. $MTR_{asym}$ analysis removes the effect of direct saturation of bulk water to reveal asymmetries in the CEST spectrum. $MTR_{asym}$ values were calculated from the Lorentzian fitting using $(S^{-\Delta\omega}-S^{\Delta\omega})/S_0$, where $S^{-\Delta\omega}$ and $S^{\Delta\omega}$ are the bulk water signal intensities at the negative and positive frequency offsets, respectively, from the bulk proton frequency referenced to 0 ppm; and $S_0$ is the bulk water signal intensity after presaturation at −5 ppm. The $MTR_{asym}$ spectrum confirmed the existence of exchangeable pools of intraliposomal water protons and also revealed increased CEST enhancement for liposomes after air exposure. One explanation for increased CEST after air exposure is that the presence of $Eu^{3+}$ chemically shifted intraliposomal water protons and added to the CEST enhancement. Another possible explanation is that oxidation to $Eu^{3+}$ decreased intraliposomal osmolality, which shrunk the liposomes and increased CEST intensity. This explanation is consistent with our observations because shrinking of liposomes through an osmotic pressure gradient is not easily detected by dynamic light scattering. The latter explanation is based on the kinetic stability of $Eu(2.2.2)^{3+}$ being lower than that of $Eu(2.2.2)^{2+}$. Accordingly, $Eu^{3+}$ is likely present as a mixture of species within the liposomes including $Eu(2.2.2)^{3+}$, $Eu^{3+}$ aqua, and phosphate complexes. A third possible explanation for the change in observed CEST is that the presence of multiple $Eu^{3+}$-containing species altered the water-permeability of the liposome membrane to increase CEST enhancement after air exposure. Investigations exploring these three possibilities, which might also explain the incomplete saturation of bulk water after air exposure, are currently underway.

Figure 8:
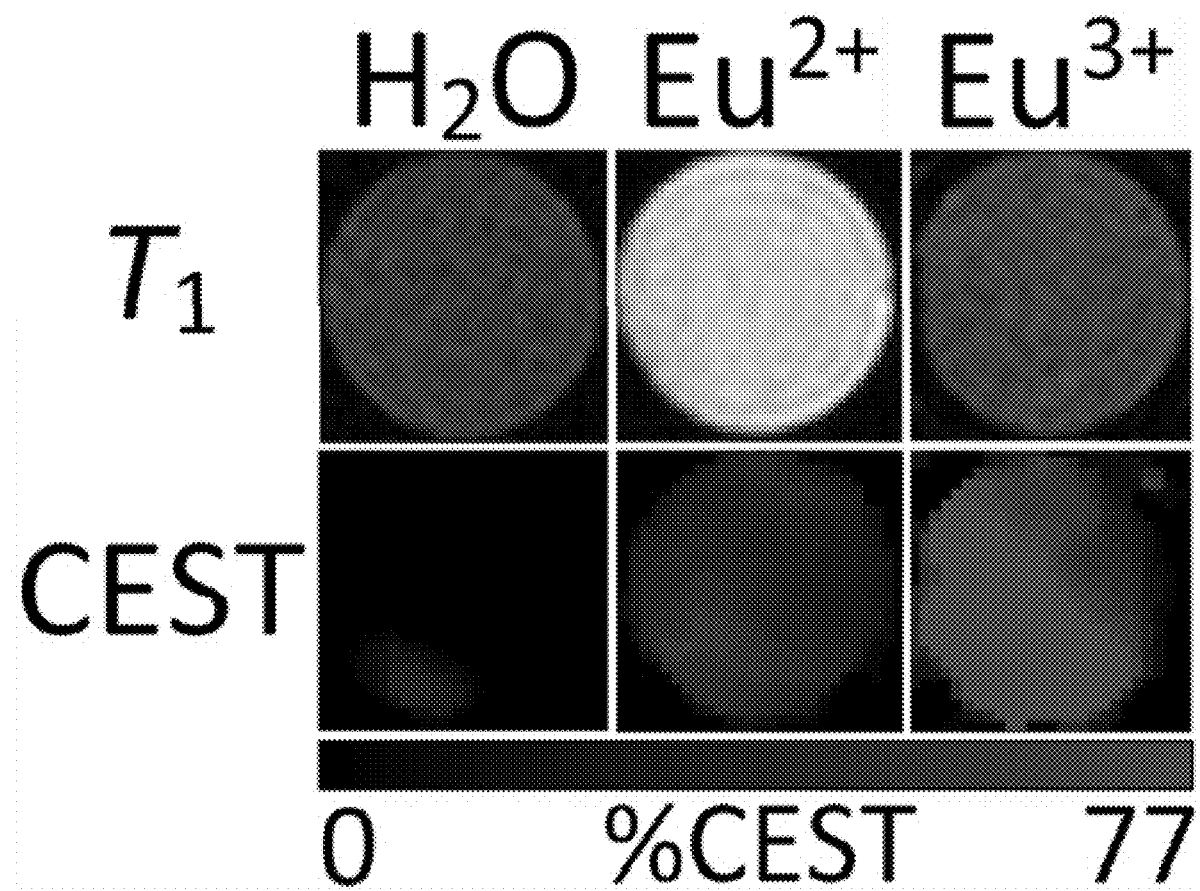
FIG. 8 provides MR phantom images (5 mm tube diameter, 7 T, and ambient temperature) of water, non-oxidized liposomes containing $Eu^{2+}$, and oxidized liposomes containing $Eu^{3+}$. The top row contains $T_1$-weighted images, and the bottom row contains CEST maps generated by subtracting presaturation at 1.2 ppm from presaturation at −1.2 ppm and dividing the difference by the presaturation at −1.2 ppm.

To visualize the nature of the $Eu^{2+/3+}$ responses, in vitro images of suspensions of the liposomes were acquired before and after exposure to air (FIG. 8). The $T_1$-weighted images confirmed positive contrast enhancement for the $Eu(2.2.2)^{2+}$-containing liposomes and also revealed no difference in signal intensity between water and the oxidized $Eu^{3+}$-containing liposomes at the 95% confidence interval (Student t test). To quantify the CEST enhancement, the phantom image intensities were used to calculate % CEST defined as $(1-M_{on}/M_{off})\times 100$, where $M_{on}$ and $M_{off}$ are the average signal intensities at the on- and off-resonance positions. The CEST map confirmed the presence of exchangeable intraliposomal water before and after oxidation and that % CEST increased from 52% to 77% after air exposure. These data demonstrate a distinct dual-mode response and reveal the oxidation state of Eu without knowledge of its concentration. With this demonstration of distinct orthogonal imaging, we envision tracking the migration of the contrast agent with $T_1$-weighted imaging. Upon disappearance of $T_1$ enhancement, the imaging mode of detection would be changed to CEST. The presence of CEST would indicate oxidation, and an absence of CEST enhancement would indicate clearance of the contrast agent. Furthermore, CEST enhancement could be used to indicate one or more specific disease states because the oxidation potential, and consequently loss of $T_1$ enhancement, of $Eu^{2+}$ is tunable through ligand structure modifications. Accordingly, our in vitro data provide a strong framework for optimizing our system for in vivo imaging.

To demonstrate that the liposomes did not leach Eu, the oxidized liposomes were filtered, and the Eu concentration of the filtrate was measured to be below the detection limit (<66 nM) of inductively coupled plasma optical emission spectroscopy.

In conclusion, embodiments of the invention provide the first oxidation-responsive dual-mode contrast agent for MRI based on the redox chemistry of Eu. Contrast enhancement in orthogonal imaging modes allows for the detection of Eu oxidation states without knowledge of contrast agent concentration. For these reasons, we expect this system to open the door for molecular imaging using the $Eu^{2+/3+}$ redox switch.

Experimental Procedures

Commercially available chemicals were of reagent-grade purity or better and were used without further purification unless otherwise noted. Water was purified using a PURELAB Ultra Mk2 water purification system (ELGA) and degassed prior to use. NMR spectroscopy and inductively coupled plasma optical emission spectroscopy (ICP-OES) analyses were performed at the Lumigen Instrument Center in the Department of Chemistry at Wayne State University. In vitro phantom imaging was performed at Henry Ford Hospital.

Inversion-recovery $T_1$ measurements were obtained using a Varian VNMRS 500 (499.48 MHz, 11.7 T) spectrometer before air exposure or after 24 h of air exposure. Deuterium oxide (300 mOsm NaCl) was added to make liposome suspensions 5% $D_2O$ (v/v) for the purpose of locking and shimming.

MRI scans were performed with a 7 T Varian small animal MRI scanner (299.44 MHz, 7.0 T) equipped with a 12 cm bore magnet and a 38 mm diameter homemade transmit/receive quadrature birdcage coil. Samples included liposomes that were not exposed to air, liposomes that were exposed to air for 24 h, and water. The $T_1$-weighted images were acquired at ambient temperature (echo time: 11 ms; repetition time: 320 ms; seven image slices at 1 mm thickness; 24×24 mm² field of view; and four averages). The liposome-encapsulated $Eu^{3+}$ (chemical exchange saturation transfer, CEST) effects were measured at ambient temperature under the same parameters used in a previous CEST MRI study. A RARE MRI pulse sequence with a RARE factor of 8 (repetition time/echo time, 4.0 s/11 ms) was applied with a 17 µT saturation power for 2 s. A total of 64 s was required to acquire a single MR image with 128×128 pixels that covered a 24×24 mm² field of view, a single slice with a thickness of 1 mm, and a single average. The water signal was measured for each phantom when saturation was applied between 5 and −5 ppm in 0.2 ppm increments to measure the CEST effect of liposomes, and FIG. 4 in the manuscript was acquired at 1.2 ppm ($S^{\Delta\omega}$) and −1.2 ppm ($S^{-\Delta\omega}$).

Varian flexible data format (FDF) files were converted to tagged image file format (TIFF) files with a MATLAB code. TIFF files were processed to produce chemical exchange saturation transfer (CEST) spectra by measuring pixel intensities with ImageJ 1.47. A magnetization transfer ratio asymmetry analysis ($MTR_{asym}$) of the Lorentzian fit was performed because the exchangeable intraliposomal proton signal partially overlapped with the bulk water proton signal. $MTR_{asym}$ was calculated using eq 1.[4]

$$MTR_{asym} = \frac{S^{-\Delta\omega} - S^{-\Delta\omega}}{S_0} \qquad \text{eq 1.}$$

In eq 1, $S^{-\Delta\omega}$ and $S^{\Delta\omega}$ are the bulk water signal intensities at the negative and positive frequency offsets, respectively, from the bulk water proton frequency referenced to 0.00 ppm; and $S_0$ is the bulk water signal intensity after presaturation at −5 ppm. Percent CEST (% CEST) was calculated using eq 2.[5]

$$\%CEST = \left(1 - \frac{M_{on}}{M_{off}}\right)100 \qquad \text{eq 2.}$$

In eq 2, Mon and Moff are the average signal intensities (calculated with ImageJ) of the same phantom tube slice at 360 Hz (1.2 ppm) and −360 Hz (−1.2 ppm), respectively. The CEST image was created by subtracting the TIFF slice at 360 Hz (1.2 ppm) from the identical slice at −360 Hz (−1.2 ppm) and the difference was divided by the slice at 360 Hz (−1.2 ppm). The % CEST scale bar was created by calibrating the pixel range of the CEST image to the maximum % CEST value obtained from eq 2 using a linear fit.

Dynamic light scattering data were obtained using a Malvern Zetasizer Nano-ZS instrument (ZEN3600) operating with a 633 nm wavelength laser. Dust was removed from samples by filtering through 0.2 µm hydrophilic filters (Millex-LG, SLLGR04NL). Liposome samples were prepared for light scattering experiments by diluting (1:10) purified liposome suspensions in iso-osmolar phosphate-buffered saline [PBS; $Na_2HPO_4$ (29 mM), $NaH_2PO_4$ (46 mM), NaCl (57 mM), and KCl (2.1 mM); pH 7.0]. For liposome size measurements with no air exposure, air-tight cuvettes were filled in a glovebox under an atmosphere of Ar.

ICP-OES measurements were acquired on a Jobin Yvon Horiba Ultima spectrometer. All samples were diluted with 2% $HNO_3$, which was also used for blank samples during calibration. The calibration curve was created using the Eu emission intensity at 381.965 nm for a 1-10 ppm concentration range (diluted from Alfa Aesar Specpure AAS standard solution, $Eu_2O_3$ in 5% $HNO_3$, 1000 µg/mL), and all samples were diluted to fall within this range.

Preparation of Hydration Solution

The hydration solution was prepared by stirring an aqueous solution of $EuCl_2$ and 4,7,13,16,21,24-hexaoxa-1,10-diazabicyclo[8.8.8]hexacosane (cryptand) for 12 h under an atmosphere of Ar followed by a phosphate-buffer-workup.[6] To account for loss of phosphate during the precipitation step of this experiment, a PBS stock solution was prepared with a high concentration of phosphate (1 M). The purpose of the high phosphate concentration was to ensure PBS buffer capacity was not lost upon phosphate precipitation in the presence of uncomplexed $Eu^{3+}$ in the oxygen-exposed samples and to maintain physiological osmolality (300 mOsm). This PBS solution was prepared in a glovebox under an atmosphere of Ar by dissolving anhydrous dibasic sodium phosphate (42.6 g, 0.300 mol), monobasic sodium phosphate monohydrate (27.6 g, 0.200 mol), sodium chloride (22.3 g, 0.381 mol), and potassium chloride (1.01 g, 13.6 mmol) in $H_2O$ (500 mL). The pH of the resulting solution was brought to 7.0 with the addition of solid sodium hydroxide (3.87 g, 96.8 mmol).

To a 4 mL glass vial equipped with a magnetic stir bar was added aqueous $EuCl_2$ (261.4 µL, 206.6 mM, 1 equiv) and aqueous cryptand (207.7 µL, 260.0 mM, 1 equiv) under an atmosphere of Ar. The resulting clear, colorless solution was stirred for 12 h before addition of PBS [60 µL; $Na_2HPO_4$ (383 mM), $NaH_2PO_4$ (617 mM), NaCl (762 mM), KCl (27.2 mM); pH 7.0] and water (670.9 µL) to bring the total volume to 1.20 mL. Upon addition of PBS, a slightly turbid suspension formed that was stirred for 1 h and then filtered through a 0.2 µm hydrophilic filter. The Eu concentration of the clear, colorless filtrate was determined by ICP-OES. This filtrate was used for liposome preparation.

Preparation of Liposomes

Liposomes were prepared via the thin-film hydration technique (Liu, G.; Liang, Y.; Bar-Shir, A.; Chan, K. W. Y.; Galpoththawela, C. S.; Bernard, S. M.; Tse, T.; Yadav, N. N.; Walczak, P.; McMahon, M. T.; Bulte, J. W. M.; van Zijl, P. C. M.; Gilad, A. A. *J. Am. Chem. Soc.* 2011, 133, 16326-16329). To a 4 mL vial was added 1-palmitoyl-2-oleoyl-sn-glycero-3-phosphocholine (22.0 mg, 2.89 µmol, 1.4 equiv), cholesterol (8.0 mg, 2.1 µmol, 1 equiv), and chloroform (1 mL) to produce a clear, colorless solution. Solvent was removed under reduced pressure to afford a visible film on the bottom of the vial. Under an atmosphere of Ar, the hydration solution (1.15 mL) and vial containing the lipid thin film were placed in a water bath at 55° C. for 30 min, and then the hydration solution was added to the vial containing the thin film. The resulting white suspension was stirred at 55° C. for 1 h. Extrusion of the suspension was accomplished using a mini-extruder and heating block (Avanti Polar Lipids, Alabaster, Ala., USA) heated to 55° C. (4 passes through a 0.2 µm polycarbonate filter followed by 15 passes through a 0.1 µm polycarbonate filter). After extrusion, the suspension was allowed to cool to ambient temperature within the Ar-filled glovebox for 1 h.

Non-encapsulated $Eu^{2+}$-containing cryptate was removed from the liposome suspension in an Ar-filled glovebox via spin filtering (Amicon Ultra regenerated cellulose 3,000 molecular weight cut off). The liposome suspension was filtered in aliquots because the volume of the suspension exceeded the volume of the spin filter. When the volume of suspension in the filter reached 0.3 mL after spinning, the volume was brought to 0.5 mL with the addition of iso-osmolar (300 mOsm) PBS prepared by dilution of the PBS solution described above. Spin-filtered fractions were collected until Eu was not detectable by ICP-OES (14 fractions).

Figure 9:
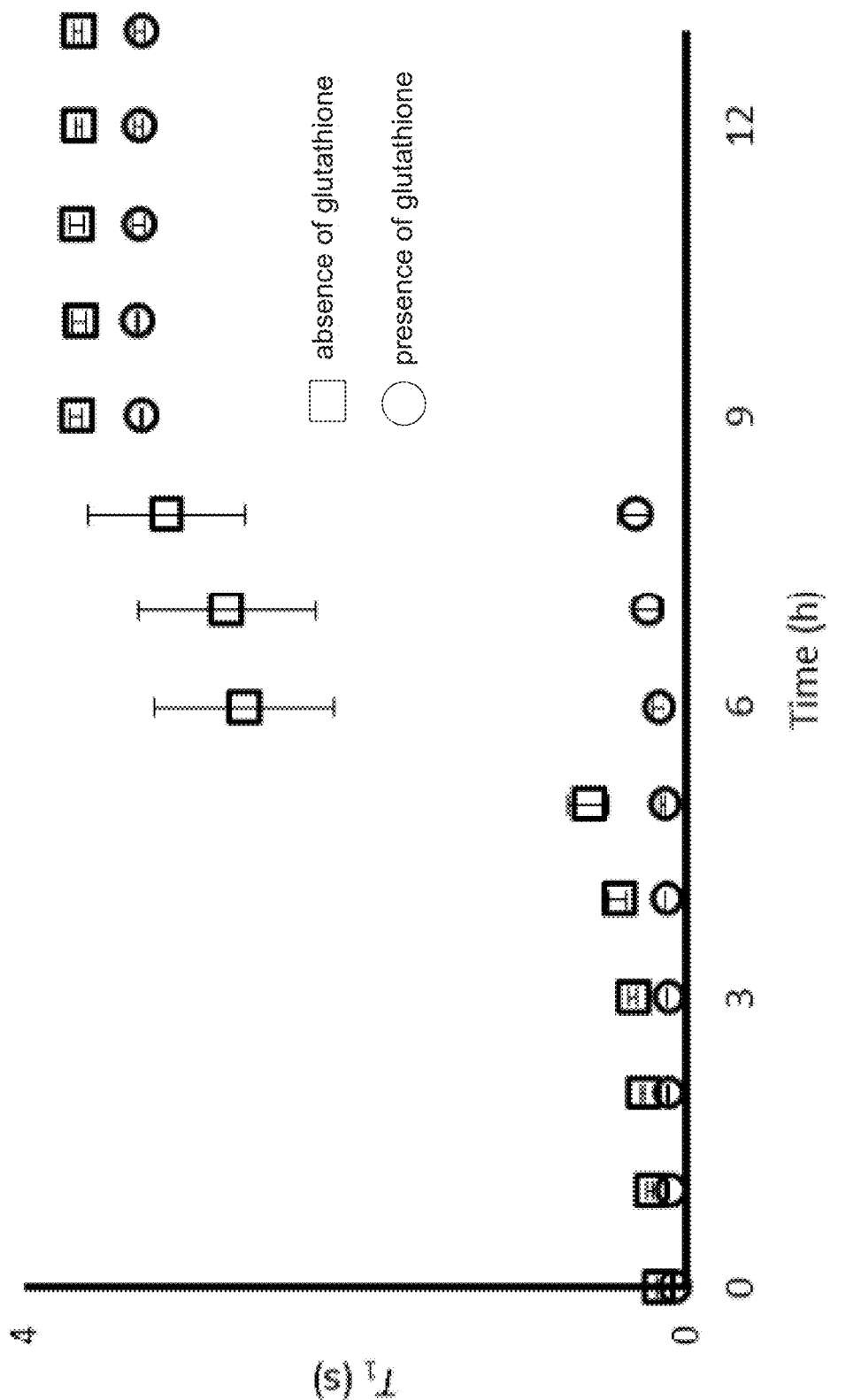
FIG. 9 provides a plot of T1 vs time of the EuII-containing complex of ligand 4 (3 mM) in the absence (□) and presence (○) of glutathione (325 mM).

FIG. 9 shows a Plot of $T_1$ vs time of the EuII-containing complex of ligand 4 (3 mM) in the absence (□) and presence (○) of glutathione (325 mM). Samples were prepared in a glovebox in the absence of molecular oxygen and then poured into an NMR tube in the air outside of the glovebox at time=0. Pouring allowed samples to become aerated. Samples were kept at 37° C. and exposed to air for the duration of the experiment. Oxidation of $Eu^{2+}$ to $Eu^{3+}$ results in an increase in the $T_1$ of the solution. Error bars represent the standard error of the mean of independently prepared samples. This data demonstrates that the antioxidant glutathione increases the oxidation half-life of the EuII-containing complex of ligand 4 by approximately 4 hours.

These results demonstrate in vivo oxidative stability and support developing positive contrast agents for ultra-high field strength MRI using $Eu^{2+}$-based complexes. These probes, based on the stabilization of $Eu^{2+}$, will be significant because they are expected to enable the use of ultra-high field strengths for imaging studies that are routinely carried out at 1.5 and 3 T, as well as new studies that require both high resolution imaging and contrast enhancement. In particular, compositions of the invention are useful at magnetic fields greater than 3 T (e.g., 7 to 11 T). The present invention represents the first step toward the use of the complexes as contrast agents at ultra-high field strengths in preclinical research and diagnostic medicine. Subsequently, these improved contrast agents are expected to facilitate earlier detection of disease when used in combination with higher field strength MRI, and early diagnoses correspond to higher rates of successful treatment. Furthermore, the $Eu^{II}$-based contrast agents will enable better monitoring of therapies, especially when both high resolution and contrast enhancement are vital for success.

General Procedure for the Synthesis of $Eu^{II}$-Containing Cryptates from Ligands A degassed aqueous solution of $EuCl_2$ (1 equiv) is mixed with a degassed aqueous solution of a cryptand (2 equiv). The resulting mixture is stirred for 12 hours at ambient temperature under Ar. Degassed PBS (10×) is added to make the entire reaction mixture 1× in PBS, and stirring is continued for 30 min. The concentration of Eu in the resulting solution is verified by ICP-MS.

Multi-Dentate Ligand Having Formula VI:

$GdCl_3.6H_2O$ (63.4 mg, 0.171 mmol) was dissolved in water (2 mL) and pH adjusted to pH 6 using NaOH. The metal solution was then added to a solution containing 1 (103 mg, 0.159 mmol) in water (4 mL), pH adjusted to 6 using NaOH. The reaction mixture was purged with argon and allowed to stir at ambient temperature for 24 h. Dialysis was performed using a 100-500 Da membrane. The dialysis water was changed three times over the course of 10 h. The solution was then transferred from the dialysis membrane to a flask, and solvent was removed under reduced pressure. A crude yield was then measured to be 134 mg, and some of this compound (5.2 mg, 0.0075 mmol) was dissolved in carbonate buffer (pH 9.8, 3 mL, 0.5 M). The resulting solution was added to a solution containing the amine-substituted cryptand (LIGAND 36 from FIG. 3, 4.8 mg, 0.011 mmol) in the same carbonate buffer (2 mL). Throughout the combination of the two solutions, the pH was monitored via pH paper and kept between 9 and 10. The reaction solution was allowed to stir at ambient temperature for 11 h. Dialysis was performed using a 100-500 Da membrane, including changing of the dialysis water 3 times over the course of 24 h. The mixture was transferred to a flask and solvent was removed under reduced pressure where a resulting crude yield was measure to be 5.5 mg. High-performance liquid chromatography (HPLC) analysis of the resulting conjugation using a PFPP column showed elution between 3.156 and 3.174 minutes using a 0-95% gradient (ramp began at 20 minutes, reached 95% at 22 minutes, and decreased at 26 minutes and reached 0% again at 28 minutes). This complex can be mixed with one equivalent of EuCl$_2$ to produce the a europium metal complex.

5,6-(4-Fluorobenzo)-4,7,13,16,21,24-hexaoxa-1,10-diazabicyclo[8.8.8]hexacos-5-ane (Ligand 4 from FIG. 3)

A 2.0 g of 4-Fluorocatechole (1 equiv, 15.6 mmol) in 20 mL of acetone was added to a solution of methyl bromo ester (3 equiv, 4.4 mL, 46.8 mmol) and potassium carbonate (3 equiv, 6.5 g, 46.8 mmol) in 100 mL of acetone for a period of 10 min under an Ar atmosphere while refluxing, and the resulting mixture was heated under reflux for 18 h under an Ar atmosphere. After the reaction, excess K$_2$CO$_3$ was removed to yield a pale red solution which was dried under reduced pressure, and the crude oil was dissolved in ethyl acetate and washed three times with 15 mL of water. The resulting organic layer was dried under reduced pressure to yield 3.75 g of a pale yellow powdery solid (yield 88%). This material (3.57 g) of 4-fluorocatechole-o,o-diacetic acid methyl ester (13.1 mmol) and 1.43 g of Dowex50WX8-200 was added to a 120 mL of water and heated under reflux at 110° C. for 24 h under an Ar atmosphere without stirring. The resulting mixture was filtered, and the resin was washed with MeOH. The filtrate was dried under reduced pressure to yield a pale yellow powdery solid, of which 0.40 g (1.8 mmol) was dissolved in thionyl chloride (5.0 mL, 68 mmol) under Ar and heated at reflux for 4 h. Excess thionyl chloride was removed under reduced pressure, and the residue was dissolved in anhydrous toluene (25 mL). The resulting solution and a solution of 1,4,10,13-tetraoxa-7,16-diazacyclooctadecane (0.32 g, 1.2 mmol, 1.0 equiv) and triethylammine (0.50 mL, 3.3 mmol, 2.4 equiv) in anhydrous toluene (25 mL) were added simultaneously (50 mL/h) to a separate flask containing anhydrous toluene (60 mL) at 0-5° C. under an Ar atmosphere. The solution was stirred for 12 h at ambient temperature. An orange suspension formed was filtered, and the solvent was removed under reduced pressure to yield a brown solid. Purification was done using silica gel chromatography (9:1 CH$_2$Cl$_2$/methanol) and yielded 0.220 g (54%) of a fluffy yellow solid. The compound (0.10 g, 0.21 mmoL, 1 equiv) was dissolved in 8.25 mL anhydrous THF, and to it was added 6.5 mL of BH$_3$-THF, 1 M solution (6.4 mmoL, 30 equiv) slowly while stirring under Ar atmosphere at 0-5° C. When the addition was done, the solution was heated under reflux for 24 h. Then the solution was treated first with 6M HCl (8.25 mL) and second with water (8.25 mL) and heated under reflux for 6 h. The solution was then basified with NH$_4$OH and removed the solvent under reduced pressure. The salt was filtered out and dried again. Purification was done using silica gel chromatography (8:1 CH$_2$Cl$_2$/methanol) to yield 0.220 g (54%) of 1 a pale yellow solid.

5,6-(4-chlorobenzo)-4,7,13,16,21,24-hexaoxa-1,10-diazabicyclo[8.8.8]hexacos-5-ane (Ligand 32 from FIG. 3)

A solution of 0.924 g of 4-chlorocatechole (1 equiv, 6.92 mmol) in 10 mL of acetone was added to a solution of methyl bromo ester (3 equiv, 1.95 mL, 20.76 mmol) and potassium carbonate (3 equiv, 2.827 g, 20 mmol) in 50 mL of acetone for a period of 10 min under Ar at reflux, and the resulting mixture was heated under reflux for 30 h under an Ar atmosphere. After the reaction, excess K$_2$CO$_3$ was filtered off and dried under reduced pressure. Purification was done using silica gel chromatography (1:1 hexanes/ethyl acetate) yielded 1.800 g (98%) of a yellow solid. The resulting material (1.05 g, 3.46 mmol) and 0.541 g of Dowex50WX8-200 were added to 40 mL of water and heated under reflux for 19 h under an Ar atmosphere without stirring. The resulting mixture was filtered and the resin was washed with MeOH. The filtrate was dried under reduced pressure to yield a pale yellow powdery solid 0.93 g (98%). Some of this material (0.344 g, 1.31 mmol) was dissolved in thionyl chloride (5.0 mL, 68 mmol) under Ar and was heated at reflux for 4 h. Excess thionyl chloride was removed under reduced pressure, and the residue was dissolved in anhydrous toluene (20 mL). The resulting solution and a solution of 1,4,10,13-tetraoxa-7,16-diazacyclooctadecane (0.340 g, 1.31 mmol, 1.0 equiv) and triethylamine (0.6 mL, 3.93 mmol, 3.0 equiv) in anhydrous toluene (20 mL) were added simultaneously (50 mL/h) to a separate flask containing anhydrous toluene (60 mL) at 0-5° C. under an Ar atmosphere. The solution was stirred for 16 h at ambient temperature. An orange suspension formed and was filtered, and the solvent was removed under reduced pressure to yield a yellow solid. Purification was done using silica gel chromatography (8:1 CH$_2$Cl$_2$/methanol) to yield 0.380 g (60%) of a pale yellow oil. The compound (0.380 g, 0.78 mmoL, 1 equiv) was dissolved in 20 mL of anhydrous THF and to it was added 20.0 mL of 1 M BH$_3$-THF (23.41 mmol, 30 equiv) slowly while stirring under an Ar atmosphere at 0-5° C. When the addition was done, the solution was warmed to room temperature and heated under reflux for 30 h. Then the solution was treated first with 6 M HCl (20 mL) and second with water (20 mL) and heated under reflux for another 6 h. The solution was then basified with NH$_4$OH, and the solvent was removed under reduced pressure. The salt was filtered out and dried again. Purification was done using silica gel chromatography (8:1 CH$_2$Cl$_2$/methanol) to yield 0.136 g (38%) of a white solid.

5,6-(4-bromobenzo)-4,7,13,16,21,24-hexaoxa-1,10-diazabicyclo[8.8.8]hexacos-5-ane (Ligand 33 from FIG. 3)

A solution of 0.608 g of 4-bromocatechole (1 equiv, 3.17 mmol) in 5 mL of acetone was added to a solution of methyl bromo ester (3 equiv, 0.9 mL, 9.52 mmol) and potassium carbonate (3 equiv, 1.32 g, 9.52 mmol) in 25 mL of acetone over a period of 5 min under an Ar atmosphere at reflux, and the resulting mixture was heated under reflux for 26 h under an Ar atmosphere. After the reaction, excess K$_2$CO$_3$ was filtered off and dried under reduced pressure. Purification was done using silica gel chromatography (1:1 hexanes/ethylacetate) to yield 0.900 g (98%) of a solid. This material (0.91 g, 3.15 mmol) and 0.36 g of Dowex50WX8-200 was added to 31 mL of water and heated under reflux for 24 h under an Ar atmosphere without stirring. The resulting mixture was filtered, and the resin was washed with MeOH. The filtrate was dried under reduced pressure to yield a white powdery solid 0.8 g (97%). Some of this material (0.29 g, 0.95 mmol) was dissolved in thionyl chloride (5.0 mL, 68 mmol) under Ar and was heated at reflux for 4 h. Excess thionyl chloride was removed under reduced pressure, and the residue was dissolved in anhydrous toluene (20 mL). The resulting solution and a solution of 1,4,10,13-tetraoxa-7,16-diazacyclooctadecane (0.251 g, 0.95 mmol, 1.0 equiv) and triethylammine (0.38 mL, 2.85 mmol, 3.0 equiv) in anhydrous toluene (20 mL) were added simultaneously (50 mL/h) to a separate flask containing anhydrous toluene (60 mL) at 0-5° C. under an Ar atmosphere. The solution was stirred for 12 h at ambient temperature. An orange suspension formed and was filtered, and the solvent was removed under reduced pressure to yield a brown solid. Purification was done using silica gel chromatography (8:1 $CH_2Cl_2$/methanol) to yield 0.367 g (73%) of a colorless oil. The resulting compound (0.367 g, 0.691 mmol, 1 equiv) was dissolved in 15 mL anhydrous THF and to it was added 20.5 mL of 1 M $BH_3$-THF (20.73 mmol, 30 equiv) slowly while stirring under an Ar atmosphere at 0-5° C. When the addition was done, the solution was warmed to room temperature and heated under reflux for 24 h. Then the solution was treated first with 6 M HCl (15 mL) and second with water (15 mL) and heated under reflux for another 6 h. The solution was then basified with $NH_4OH$ and the solvent was removed under reduced pressure. The salt was filtered out and dried again. Purification was done using silica gel chromatography (8:1 $CH_2Cl$/methanol) to yielded 0.220 g (54%) of a white solid.

5,6-(4-methylbenzo)-4,7,13,16,21,24-hexaoxa-1,10-diazabicyclo[8.8.8]hexacos-5-ane (Ligand 35 from FIG. 3)

A solution of 0.990 g of 4-methylcatechole (1 equiv, 7.73 mmol) in 18 mL of acetone was added to a solution of methyl bromo ester (3 equiv, 2.2 mL, 23.2 mmol) and potassium carbonate (3 equiv, 3.21 g, 23.2 mmol) in 90 mL of acetone for a period of 15 min under an Ar atmosphere and reflux, and the resulting mixture was heated under reflux for 26 h under an Ar atmosphere. After the reaction, excess $K_2CO_3$ was filtered off and dried under reduced pressure. Purification was done using silica gel chromatography (1:1 hexanes/ethyl acetate) to yield 1.617 g (76%) of a yellow oil. This material (6.03 mmol) and 0.870 g of Dowex50WX8-200 was added to 60 mL of water and heated under reflux for 29 h under an Ar atmosphere without stirring. The resulting mixture was filtered, and the resin was washed with MeOH. The filtrate was dried under reduced pressure to yield an orange powdery solid 1.669 g (97%). Some of this material (0.449 g, 1.62 mmol) was dissolved in thionyl chloride (5 mL, 68 mmol) under Ar and was heated at reflux for 4 h. Excess thionyl chloride was removed under reduced pressure, and the residue was dissolved in anhydrous toluene (20 mL). The resulting solution and a solution of 1,4,10,13-tetraoxa-7,16-diazacyclooctadecane (0.425 g, 1.62 mmol, 1.0 equiv) and triethylammine (0.66 mL, 4.9 mmol, 3.0 equiv) in anhydrous toluene (20 mL) were added simultaneously (50 mL/h) to a separate flask containing anhydrous toluene (60 mL) at 0-5° C. under an Ar atmosphere. The solution was stirred for 18 h at ambient temperature. An orange suspension formed and was filtered, and the solvent was removed under reduced pressure to yield a solid. Purification was done using silica gel chromatography (8:1 $CH_2Cl_2$/methanol) to yield 0.480 g (64%) of a pale yellow solid. The resulted compound (0.480 g, 1.03 mmol, 1 equiv) was dissolved in 20 mL anhydrous THF and was added 20 mL of 1 M $BH_3$-THF (20.60 mmol, 20 equiv) slowly while stirring under Ar atmosphere at 0-5° C. When the addition was done, the solution was warmed to room temperature and heated under reflux for 26 h. Then the solution was treated first with 6M HCl (20 mL) and second with water (20 mL) and heated under reflux at 90° C. for another 14 h. The solution was then basified with $NH_4OH$ and removed the solvent under reduced pressure. The salt was filtered out and dried again. Purification was done using silica gel chromatography (8:1 $CH_2Cl_2$/methanol) to yield 0.143 g (32%) of solid.

Carboxylated Europium Complex:

4-Isothiocyanato-1,2-benzenediacarboxylic acid (1 equiv) is dissolved in carbonate buffer (pH 9.8, 3 mL, 0.5 M). The resulting solution is added to a solution containing the amine-substituted cryptand (LIGAND 36 from FIG. 3, 1 equiv) in the same carbonate buffer (2 mL). Throughout the combination of the two solutions, the pH is monitored via pH paper and kept between 9 and 10. The reaction solution is allowed to stir at ambient temperature for 11 h. Dialysis is performed using a 100-500 Da membrane, including changing of the dialysis water 3 times over the course of 24 h. The mixture is transferred to a flask and solvent is removed under reduced pressure. The resulting ligand has the following formula:

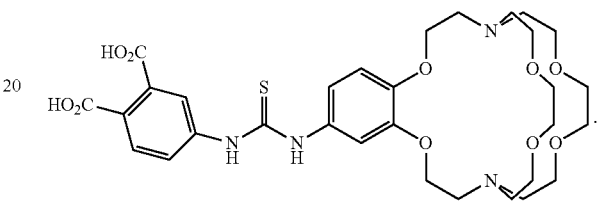

This complex is mixed with one equivalent of $EuCl_2$ to produce the final complex.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A europium metal complex comprising a europium metal atom, a multi-dentate ligand having formula (VIII), and if necessary counter-ions to maintain charge neutrality:

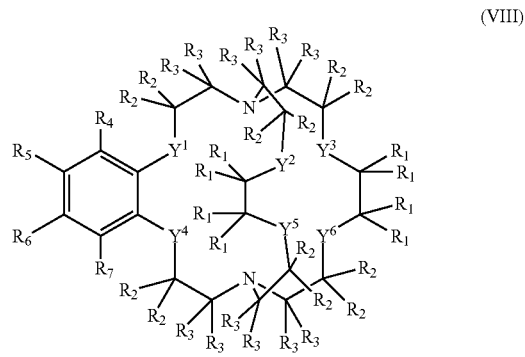

(VIII)

wherein:

$Y^1$, $Y^2$, $Y^3$, $Y^4$, $Y^5$ and $Y^6$ are each independently O or S;

$R_1$, $R_2$, $R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom;

R is H or $C_{1-12}$ alkyl; and $R_4$, $R_5$, $R_7$ are each independently hydrogen, cyano, nitro, Cl, F, Br, I, $NH_2$, $C_{6-15}$ aryl, carboxylated $C_{6-18}$ aryl, $C_{5-15}$ heteroaryl, carboxylated $C_{5-18}$ heteroaryl, $C_{1-12}$ alkyl, carboxylated phenyl, carboxylated $C_{2-12}$ alkyl, —$CO_2H$, —$CH_2CO_2H$,

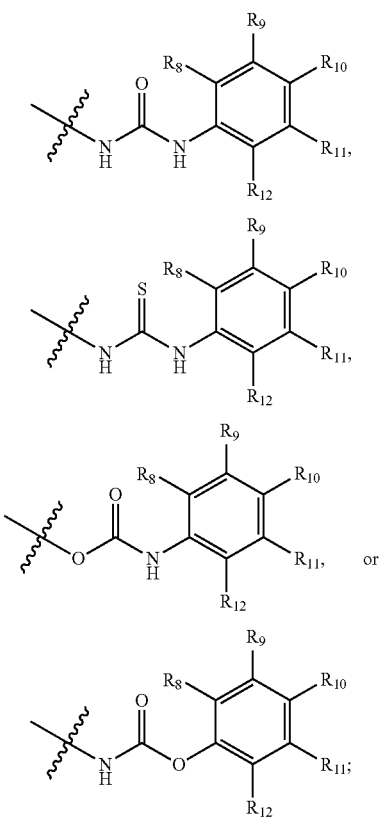

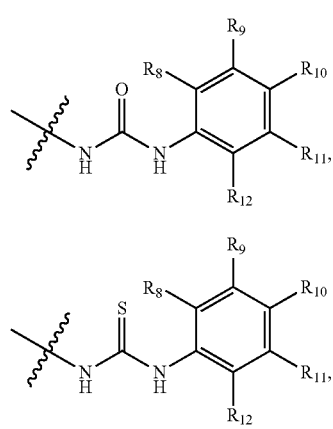

$R_6$ is $C_{6-15}$ aryl, carboxylated $C_{6-18}$ aryl, $C_{5-15}$ heteroaryl, carboxylated $C_{5-18}$ heteroaryl, carboxylated phenyl, carboxylated $C_{2-12}$ alkyl,

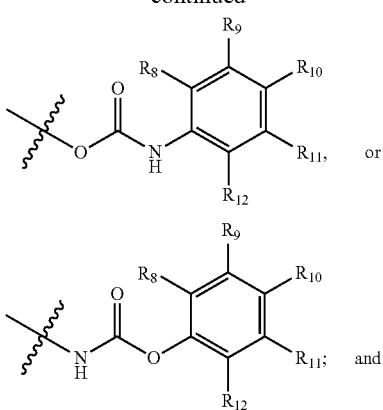

$R_8$, $R_9$, $R_{10}$, $R_{11}$, $R_{12}$ are each independently H or $CO_2H$.

2. The europium metal complex of claim 1 wherein $R_4$, $R_5$, $R_7$ are each independently hydrogen, cyano, nitro, NH2, $C_{6-15}$ aryl, carboxylated $C_{6-18}$ aryl, $C_{5-15}$ heteroaryl, carboxylated $C_{5-18}$ heteroaryl, $C_{1-12}$ alkyl, phenyl, carboxylated phenyl, carboxylated $C_{2-12}$ alkyl, —$CO_2H$, —$CH_2CO_2H$,

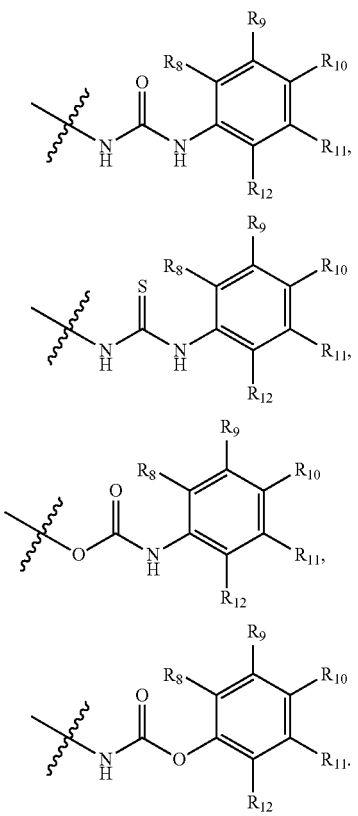

3. The europium metal complex of claim 2 wherein $Y^1$, $Y^2$, $Y^3$, $Y^4$, $Y^5$ and $Y^6$ are each independently O.

4. The europium metal complex of claim 1 wherein $R_4$, $R_5$, $R_7$ are each independently hydrogen, $C_{6-15}$ aryl, carboxylated $C_{6-18}$ aryl, $C_{5-15}$ heteroaryl, carboxylated $C_{5-18}$ heteroaryl, $C_{1-12}$ alkyl, phenyl, carboxylated $C_{2-12}$ alkyl, —$CO_2H$, —$CH_2CO_2H$,

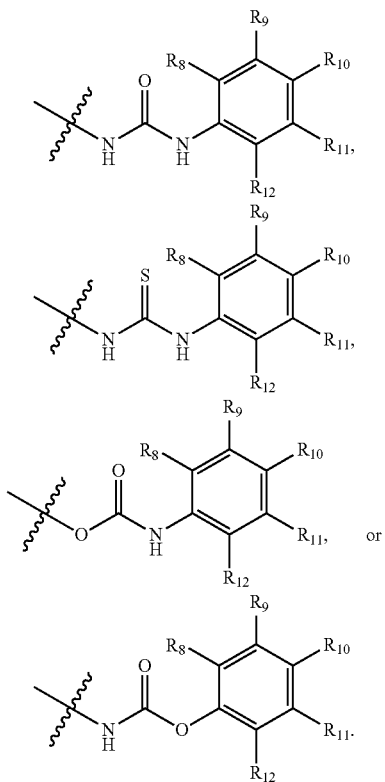

5. The europium metal complex of claim 1 wherein $R_6$ is independently

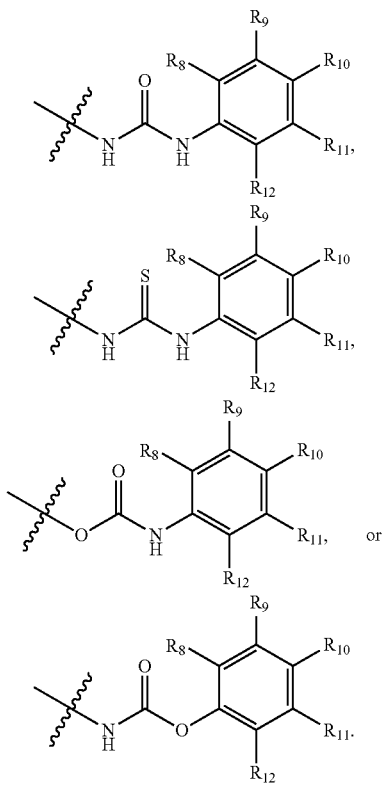

6. The europium metal complex of claim 3 wherein $R_5$ is cyano, nitro, Cl, F, Br, I, $CH_3$, $NH_2$, $C_{6-15}$ aryl, carboxylated $C_{6-18}$ aryl, $C_{5-15}$ heteroaryl, carboxylated $C_{5-18}$ heteroaryl, $C_{1-12}$ alkyl, phenyl, carboxylated phenyl, carboxylated $C_{2-12}$ alkyl, $-CO_2H$, $-CH_2CO_2H$,

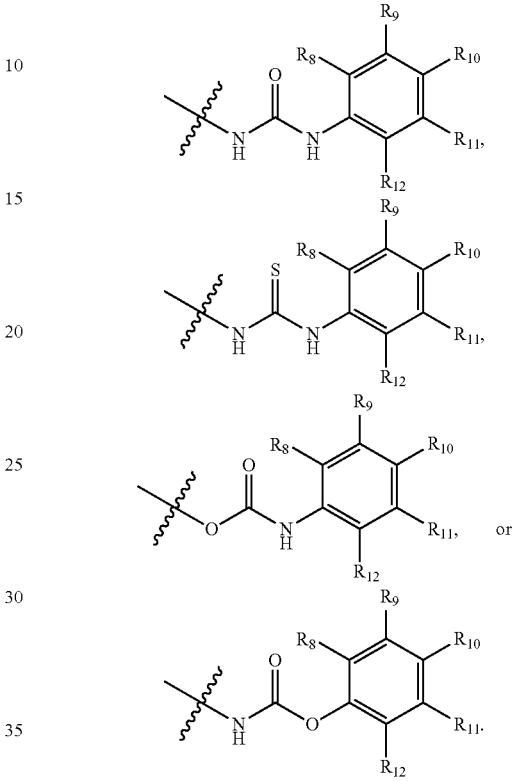

7. The europium metal complex of claim 1 wherein $R_4$, $R_5$, $R_7$ are each independently hydrogen, $-CH_3$, $-NH_2$, phenyl, carboxylated $C_{2-12}$ alkyl, $-CO_2H$, or $-CH_2CO_2H$, and R6 is $-CH_3$, $-NH_2$, phenyl, carboxylated $C_{2-12}$ alkyl, $-CO_2H$, or $-CH_2CO_2H$.

8. The europium metal complex of claim 1 wherein $R_6$ is $C_{6-15}$ aryl, carboxylated $C_{6-18}$ aryl, $C_{5-15}$ heteroaryl, carboxylated $C_{5-18}$ heteroaryl, carboxylated phenyl, or carboxylated $C_{2-12}$ alkyl.

9. The europium metal complex of claim 1 wherein $R_6$ is

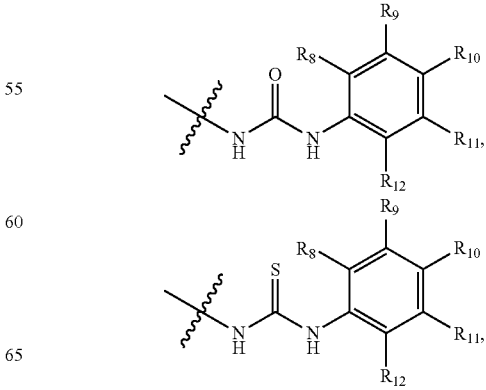

-continued
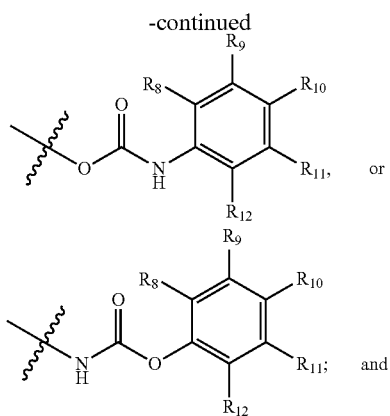
or
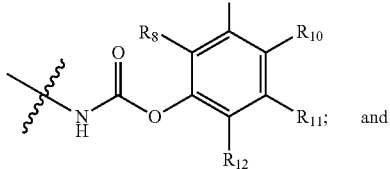
and
$R_8$, $R_9$, $R_{10}$, $R_{11}$, $R_{12}$ are each independently H or $CO_2H$.
* * * * *